(12) United States Patent
Moon et al.

(10) Patent No.: US 11,123,436 B2
(45) Date of Patent: Sep. 21, 2021

(54) METHOD OF PREPARING PHYSIOLOGICALLY ACTIVE POLYPEPTIDE CONJUGATE

(71) Applicant: HANMI PHARM. CO., LTD., Hwaseong-si (KR)

(72) Inventors: Sun Jin Moon, Hwaseong-si (KR); Cheong Byeol Shin, Hwaseong-si (KR); Sung Hee Hong, Hwaseong-si (KR); Dae Jin Kim, Hwaseong-si (KR); Se Chang Kwon, Hwaseong-si (KR)

( * ) Notice: Subject to any disclaimer, the term of this patent is extended or adjusted under 35 U.S.C. 154(b) by 27 days.

(21) Appl. No.: 15/747,141

(22) PCT Filed: Jul. 22, 2016

(86) PCT No.: PCT/KR2016/008050
§ 371 (c)(1),
(2) Date: Jan. 23, 2018

(87) PCT Pub. No.: WO2017/018742
PCT Pub. Date: Feb. 2, 2017

(65) Prior Publication Data
US 2018/0214562 A1    Aug. 2, 2018

(30) Foreign Application Priority Data

Jul. 24, 2015 (KR) .......................... 10-2015-0105310

(51) Int. Cl.
| C07K 1/30 | (2006.01) |
| A61K 47/60 | (2017.01) |
| C07K 14/605 | (2006.01) |
| C07K 14/52 | (2006.01) |
| C07K 14/59 | (2006.01) |
| C07K 14/62 | (2006.01) |

(52) U.S. Cl.
CPC ................ *A61K 47/60* (2017.08); *C07K 1/30* (2013.01); *C07K 14/52* (2013.01); *C07K 14/59* (2013.01); *C07K 14/605* (2013.01); *C07K 14/62* (2013.01); *C07K 2319/30* (2013.01)

(58) Field of Classification Search
None
See application file for complete search history.

(56) References Cited

U.S. PATENT DOCUMENTS

| 2007/0041967 A1 | 2/2007 | Jung et al. | |
| 2012/0003712 A1 | 1/2012 | Song et al. | |
| 2014/0296475 A1* | 10/2014 | Kim ....................... | C07K 14/62 530/303 |

FOREIGN PATENT DOCUMENTS

| CN | 102112493 A | 6/2011 |
| CN | 102369209 A | 3/2012 |
| CN | 104271604 A | 1/2015 |
| KR | 10-0725314 B1 | 6/2007 |
| KR | 10-0725315 B1 | 6/2007 |
| KR | 10-0775343 B1 | 11/2007 |
| KR | 10-0824505 B1 | 2/2008 |
| KR | 10-2009-0008151 A | 1/2009 |
| KR | 10-2010-0105494 A | 9/2010 |
| KR | 10-1164453 B1 | 7/2012 |
| WO | WO-01/57084 A1 | 8/2001 |
| WO | WO-2010/011096 A2 | 1/2010 |
| WO | 2010107256 A2 | 9/2010 |
| WO | WO-2013/133659 A1 | 9/2013 |
| WO | WO-2014/133324 A1 | 9/2014 |

OTHER PUBLICATIONS

Eli-Lilly package insert for Glucagon, https://web.archive.org/web/20060813080744/http://pi.lilly.com/us/rglucagon-pi.pdf, available online 2006.*
Reynolds, Fred et al, "Method of determining nanoparticle core weight." Anal. Chem. (2005) 77 p. 814-817.*
The Peptide 2.0 FAQ page, https://www.peptide2.com/peptide_synthesis_frequently_asked_questions.php, downloaded Nov. 28, 2018.*
Atha, Donald H. and Ingham, Kenneth C., "Mechanism of precipitation of proteins by polyethylene glycols." J. Biol. Chem. (1981) 256(23) p. 12108-12117.*
The Abbiotec catalog page for the peptide, https://www.abbiotec.com/peptides/exendin-4-peptide, downloaded Nov. 28, 2018.*
Ball, Stephan et al, "Investigation into the alternatives to acetonitrile for the analysis of peptides on a septech st150 10-c18." Agilent Technologies application note 5990-7951EN, published 2011.*
Laysan Bio FAQ page http://laysanbio.com/index.php?src=gendocs&link=FAQ&category=Main, downloaded Nov. 28, 2018.*
Vilsboll, Tina; "Liraglutide: a human glp-1 analog for type 2 diabetes." Therapy (2009) 6(2) p. 199-207.*
Lovrien, R.E. et al. (2001). "Selective Precipitation of Proteins," *Current Protocols in Protein Science Supplement 7*, Unit 4.5, Table 4.5.1; Figure 4.5.2.

* cited by examiner

*Primary Examiner* — Fred H Reynolds
(74) *Attorney, Agent, or Firm* — Morrison & Foerster LLP

(57) ABSTRACT

Provided is a method of preparing a physiologically active polypeptide conjugate, in which a physiologically active polypeptide and a non-peptidyl polymer are linked to each other via a covalent bond. The method is to improve an overall yield of the physiologically active polypeptide conjugate by improving a reaction of the non-peptidyl polymer and the physiologically active polypeptide, and particularly, the method is to prepare a physiologically active polypeptide conjugate in a high yield by performing a two-step reaction through selective precipitation. The preparation method of the present invention is used to produce a non-peptidyl polymer-physiologically active polypeptide conjugate and a physiologically active polypeptide-physiologically active carrier conjugate in a high yield, and therefore, the method may be used in the development of long-acting formulations of various peptide drugs which maintain in vivo activity at a relatively high level and have remarkably increased blood half-life.

17 Claims, 19 Drawing Sheets

[Fig. 1]
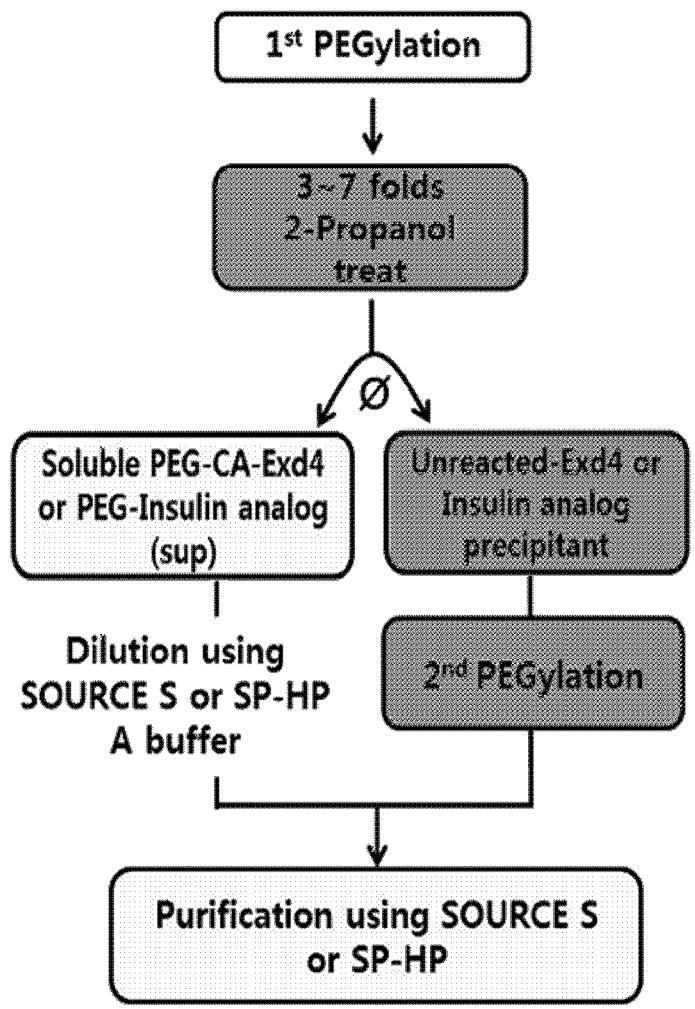

[Fig. 2]
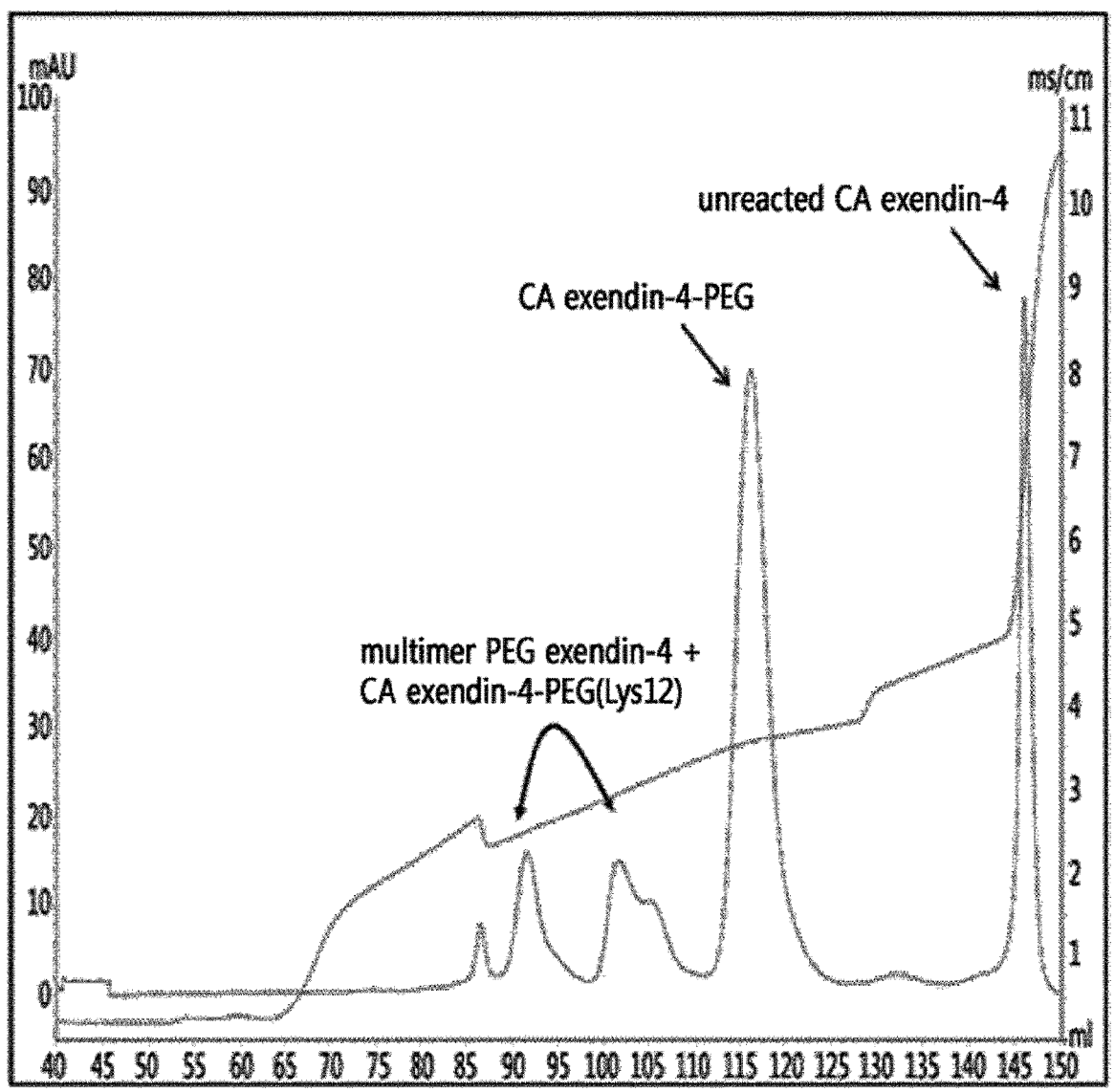

[Fig. 3]
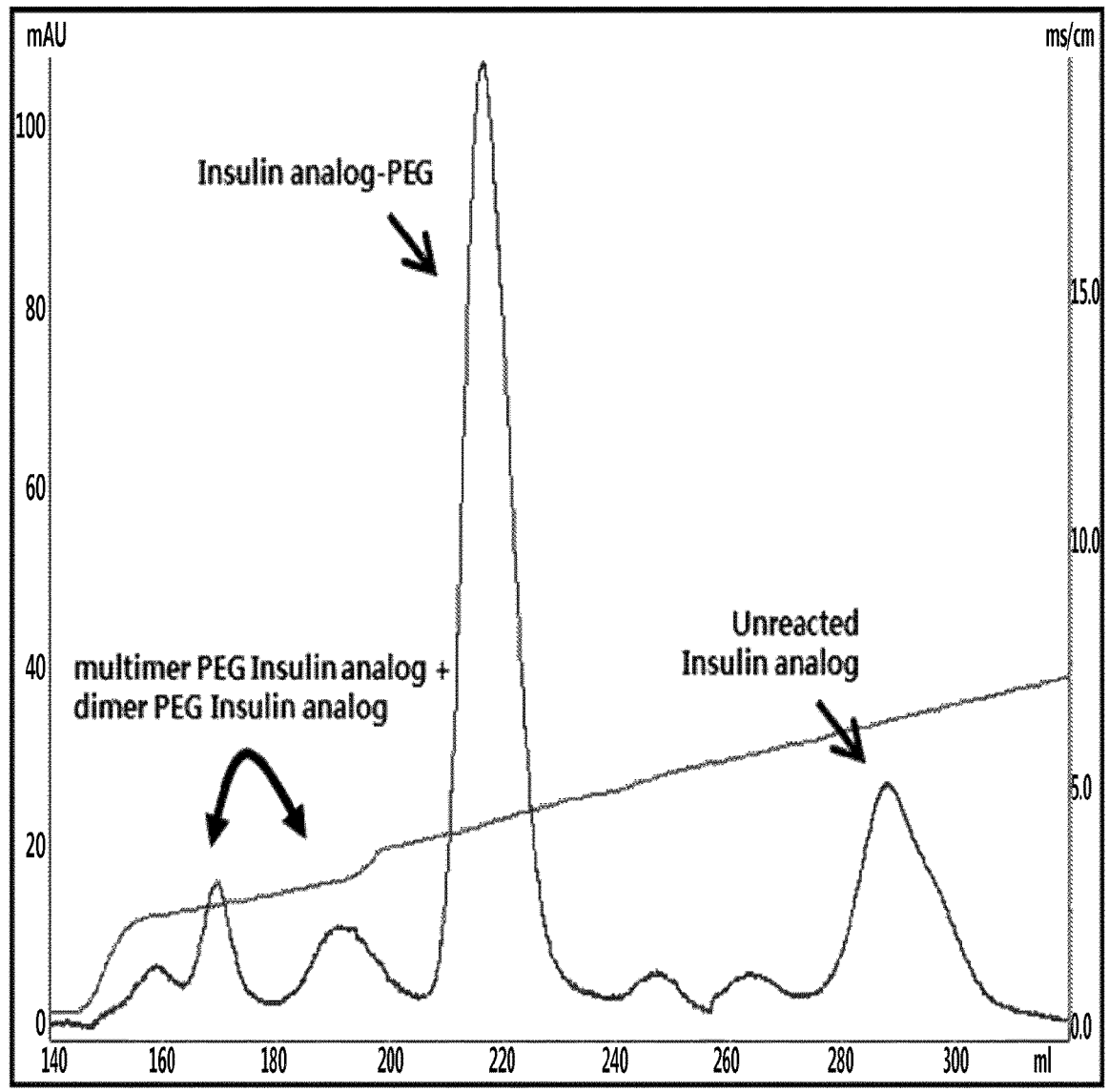

[Fig. 4]
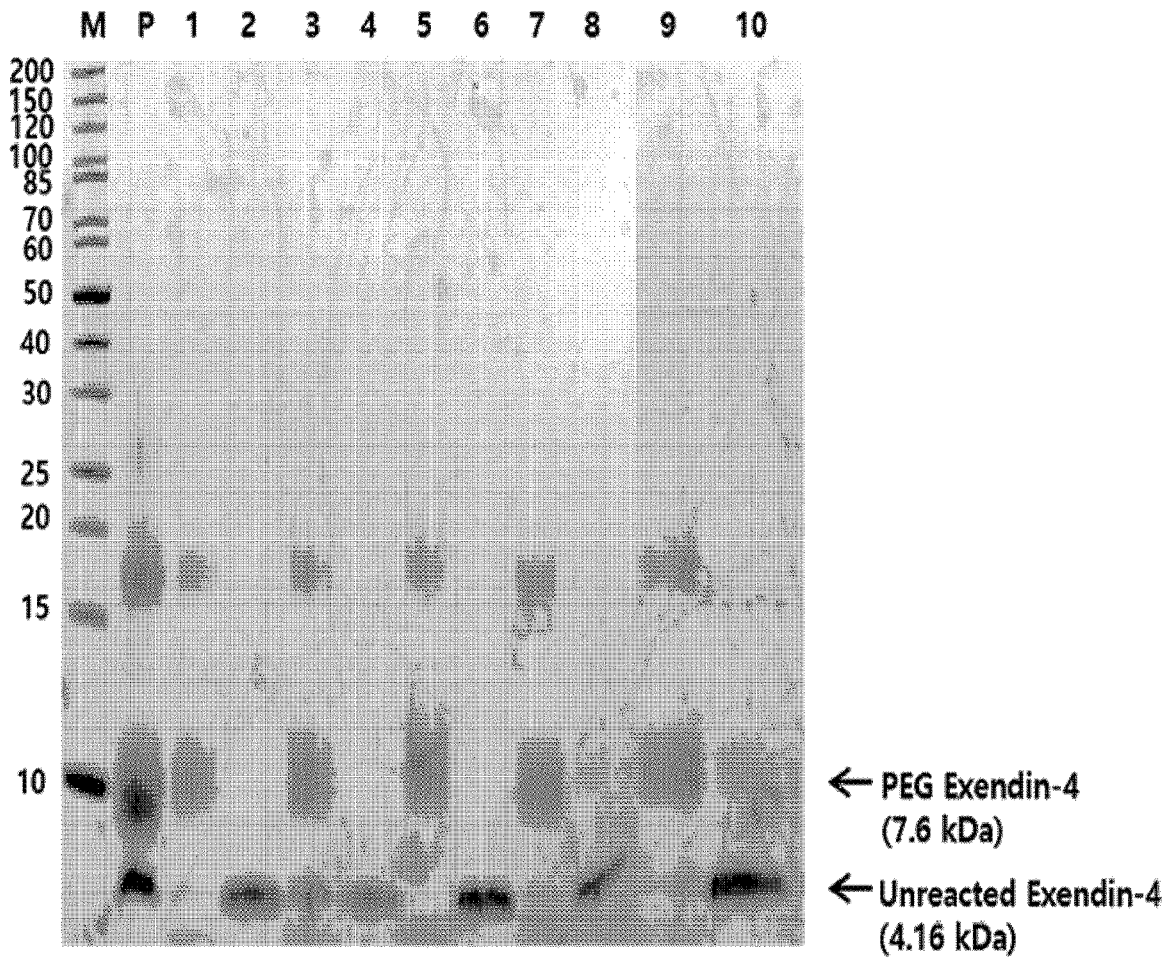

[Fig. 5]

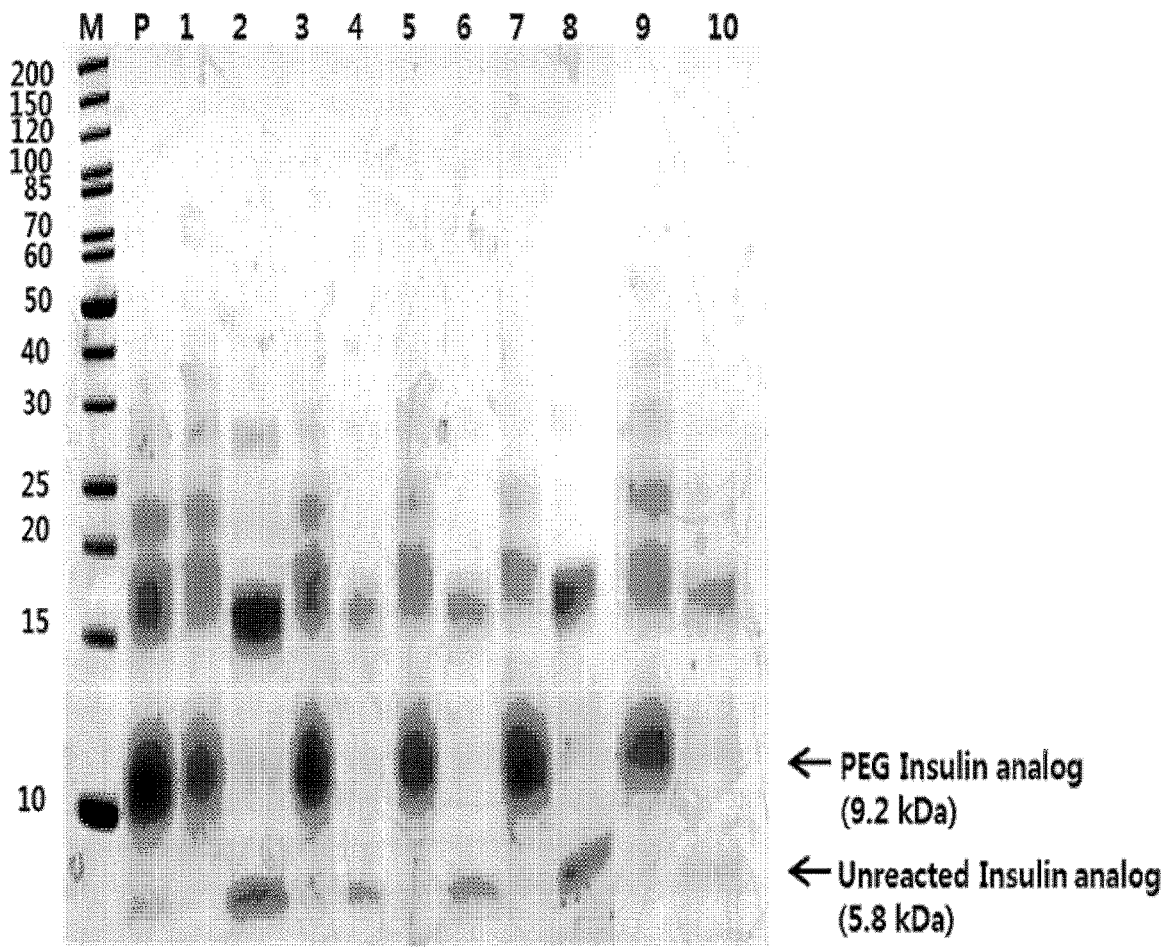

← PEG Insulin analog (9.2 kDa)
← Unreacted Insulin analog (5.8 kDa)

M: Marker   P: 1st PEGylation reaction solution
1: Aqueous solution after adding isopropanol to the reaction mixture
2: Precipitate after adding isopropanol to the reaction mixture
3: Aqueous solution after adding ethanol to the reaction mixture
4: Precipitate after adding ethanol to the reaction mixture
5: Aqueous solution after adding 1-propanol to the reaction mixture
6: Precipitate after adding 1-propanol to the reaction mixture
7: Aqueous solution after adding acetone to the reaction mixture
8: Precipitate after adding acetone to the reaction mixture
9: Aqueous solution after adding acetonitrile to the reaction mixture
10: Precipitate after adding acetonitrile to the reaction mixture

[Fig. 6]
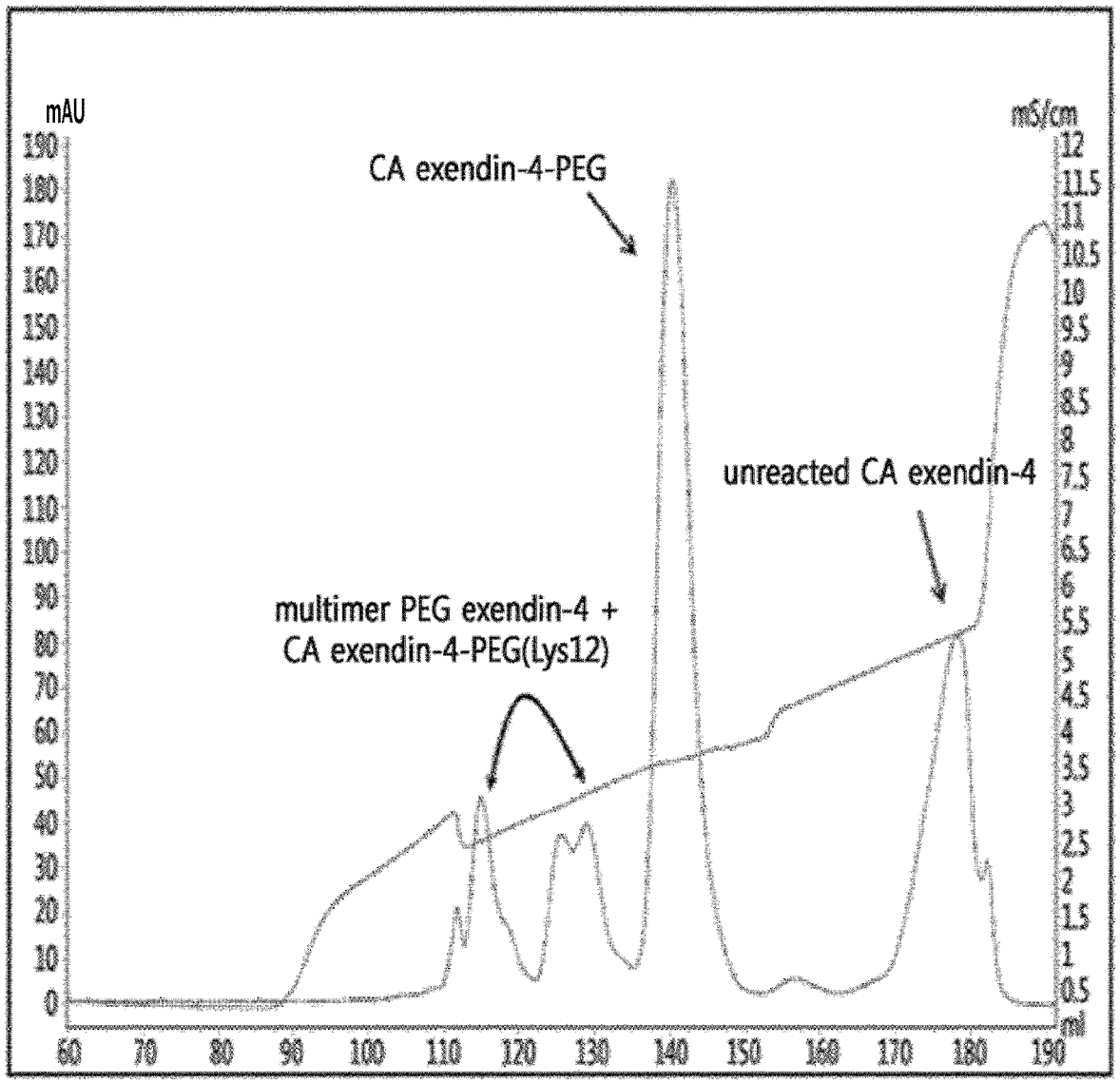

[Fig. 7]
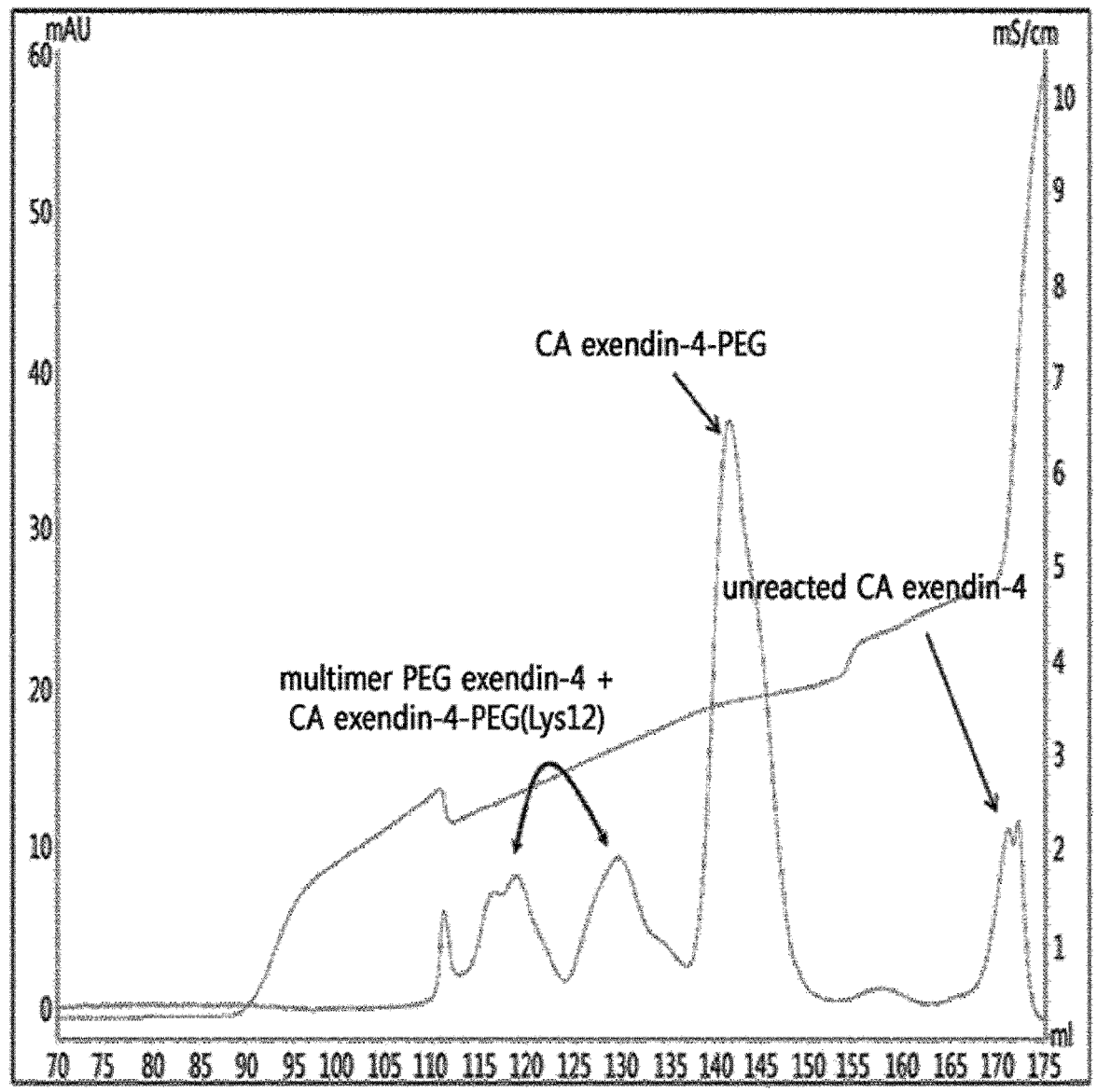

[Fig. 8]
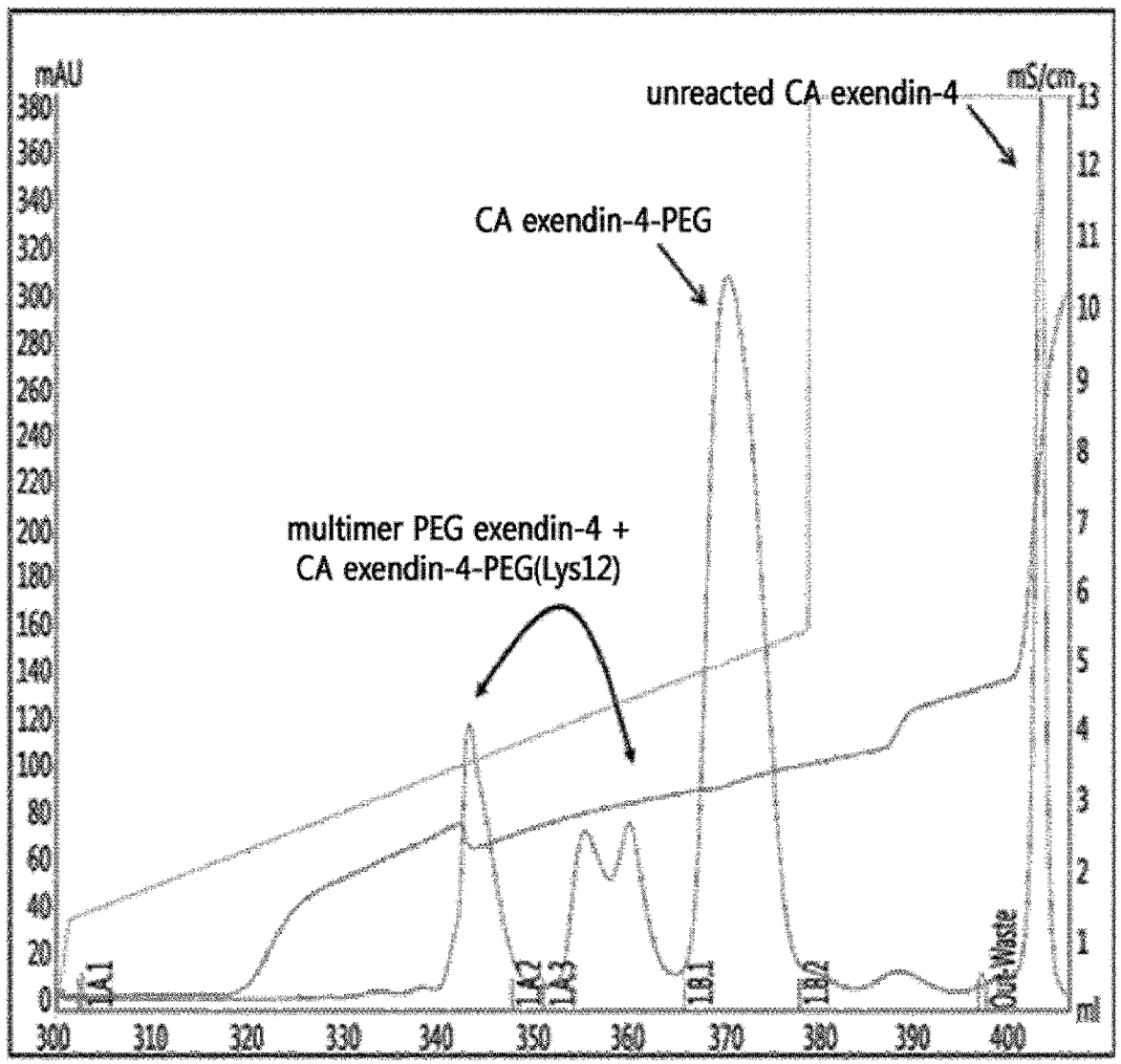

[Fig. 9]
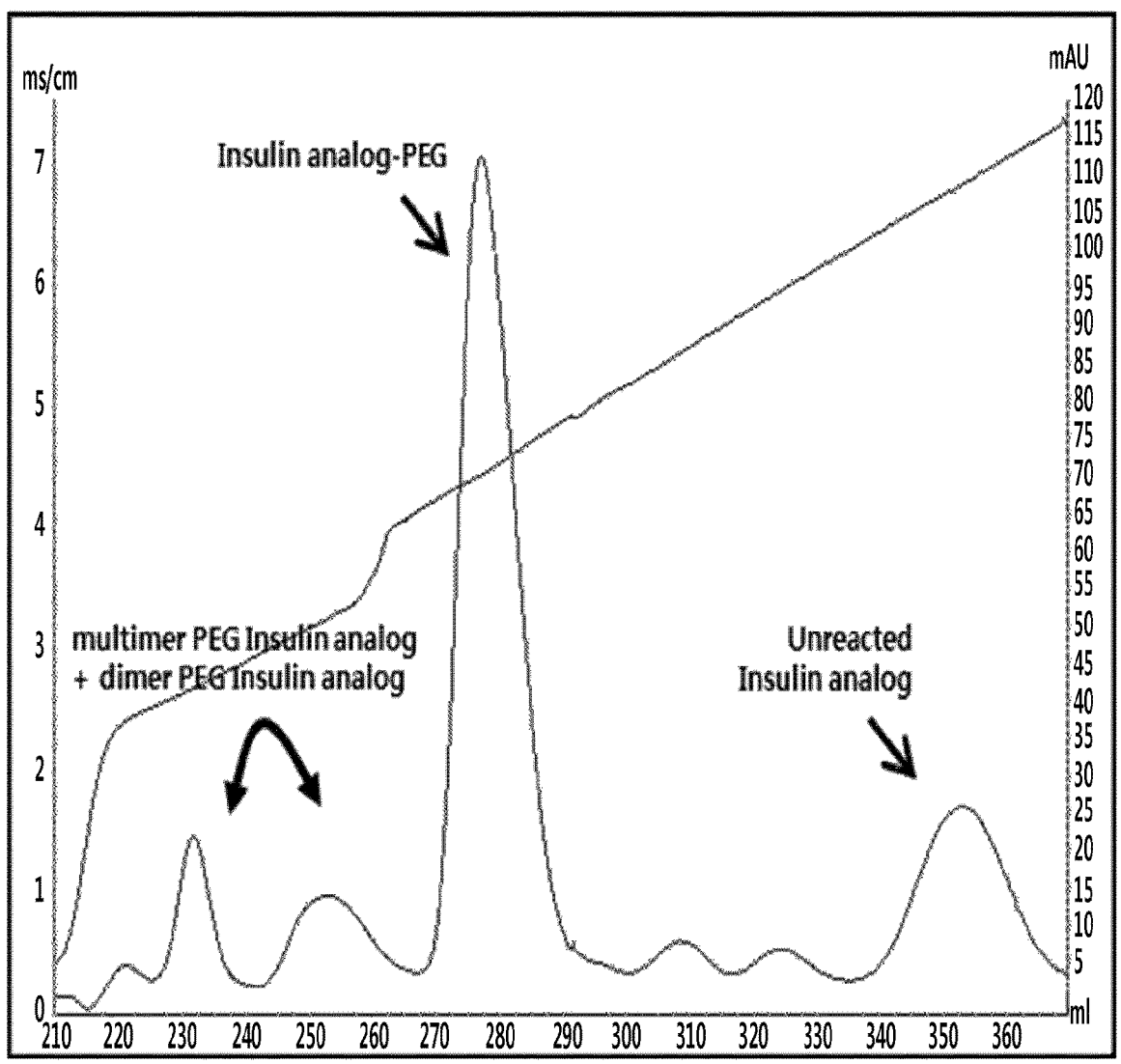

[Fig. 10]
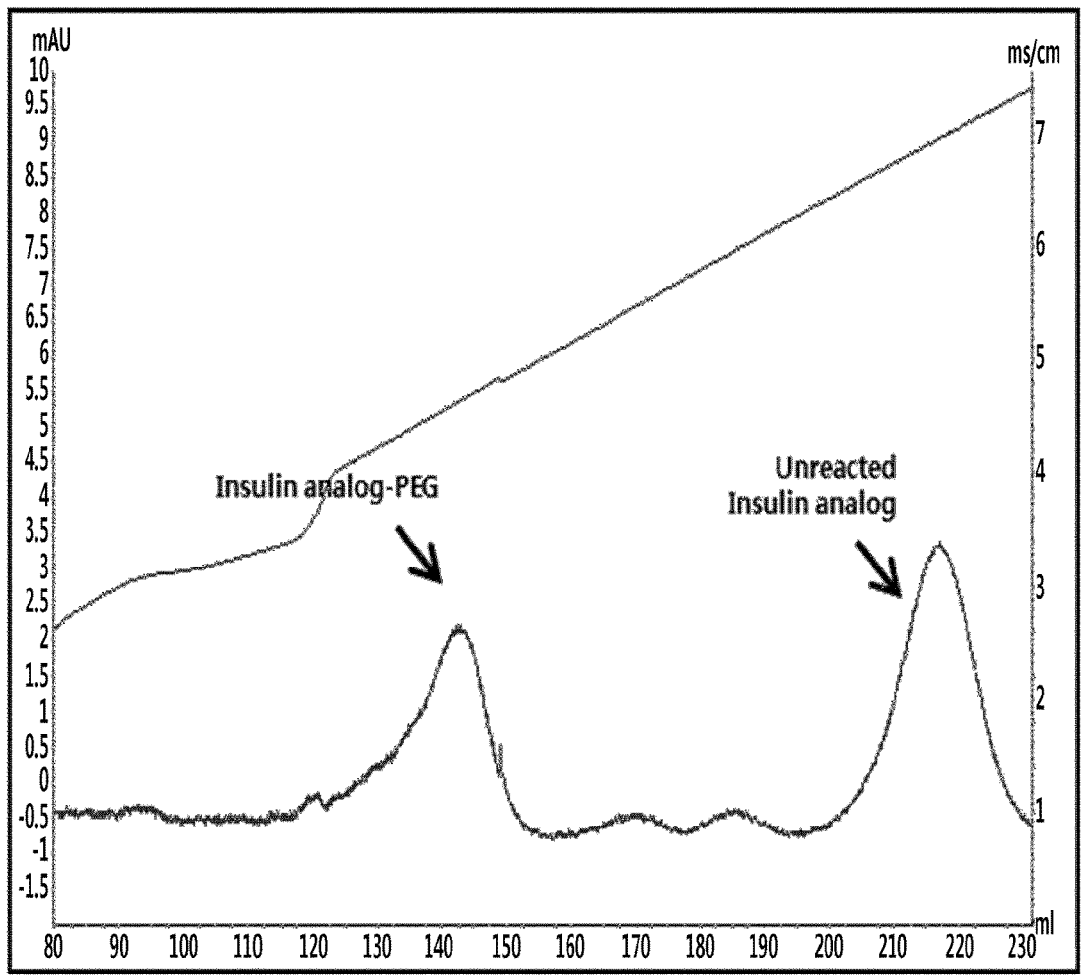
[Fig. 11]
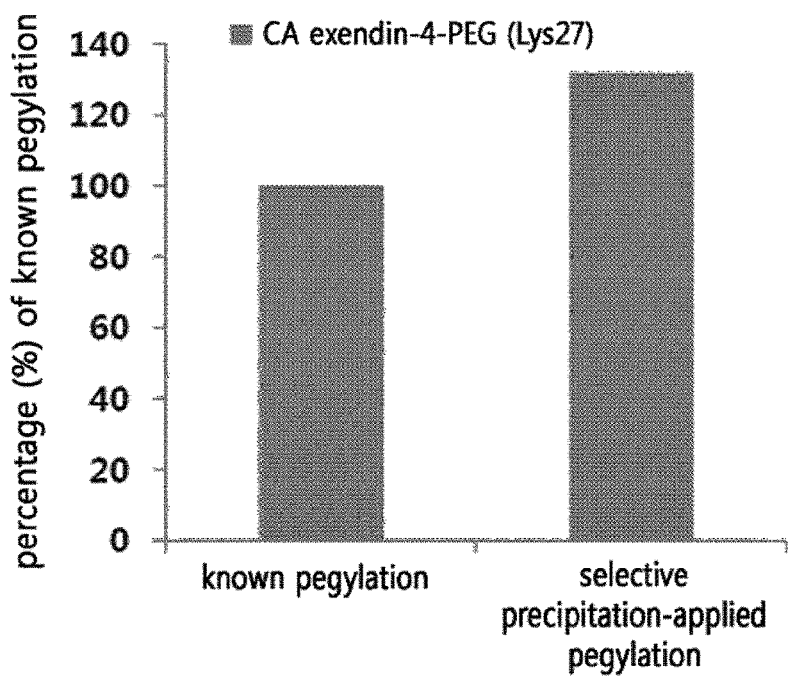

[Fig. 12]
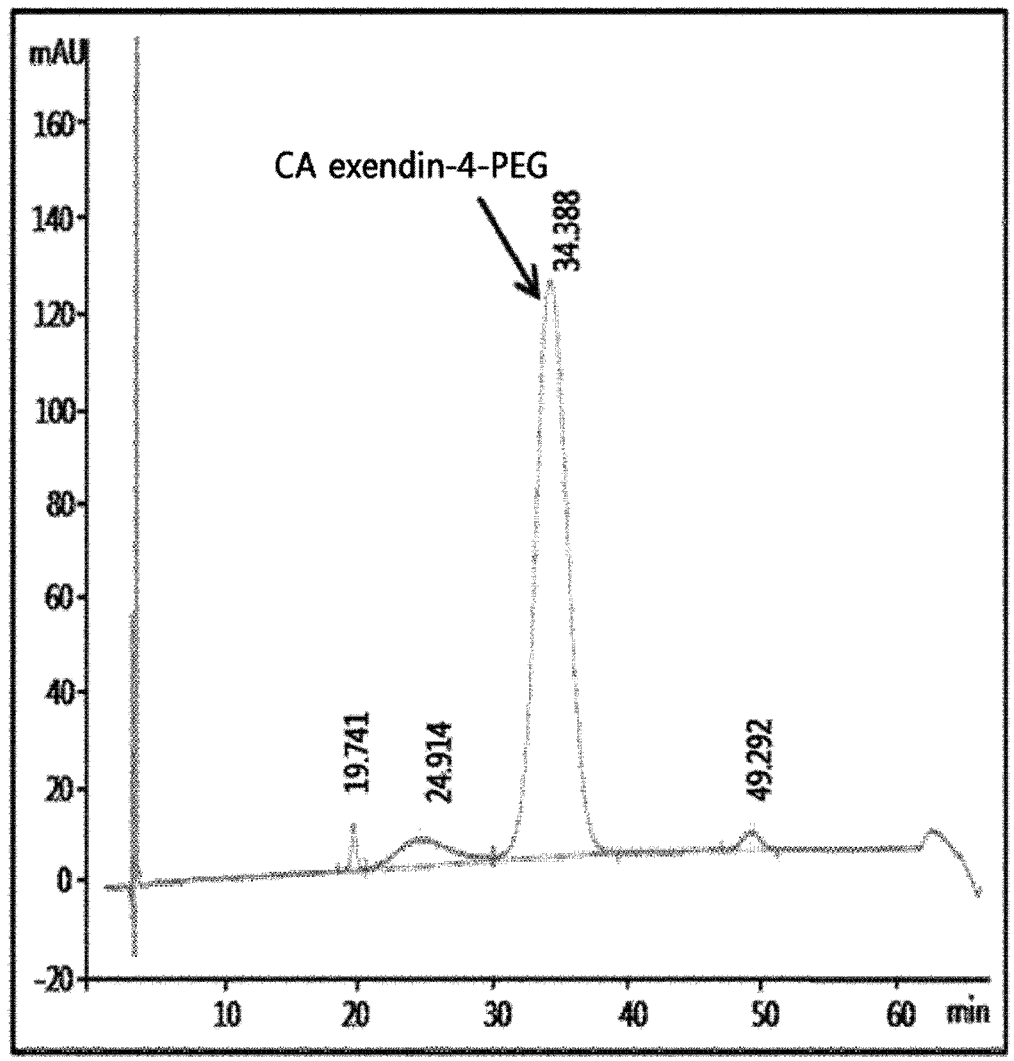

[Fig. 13]
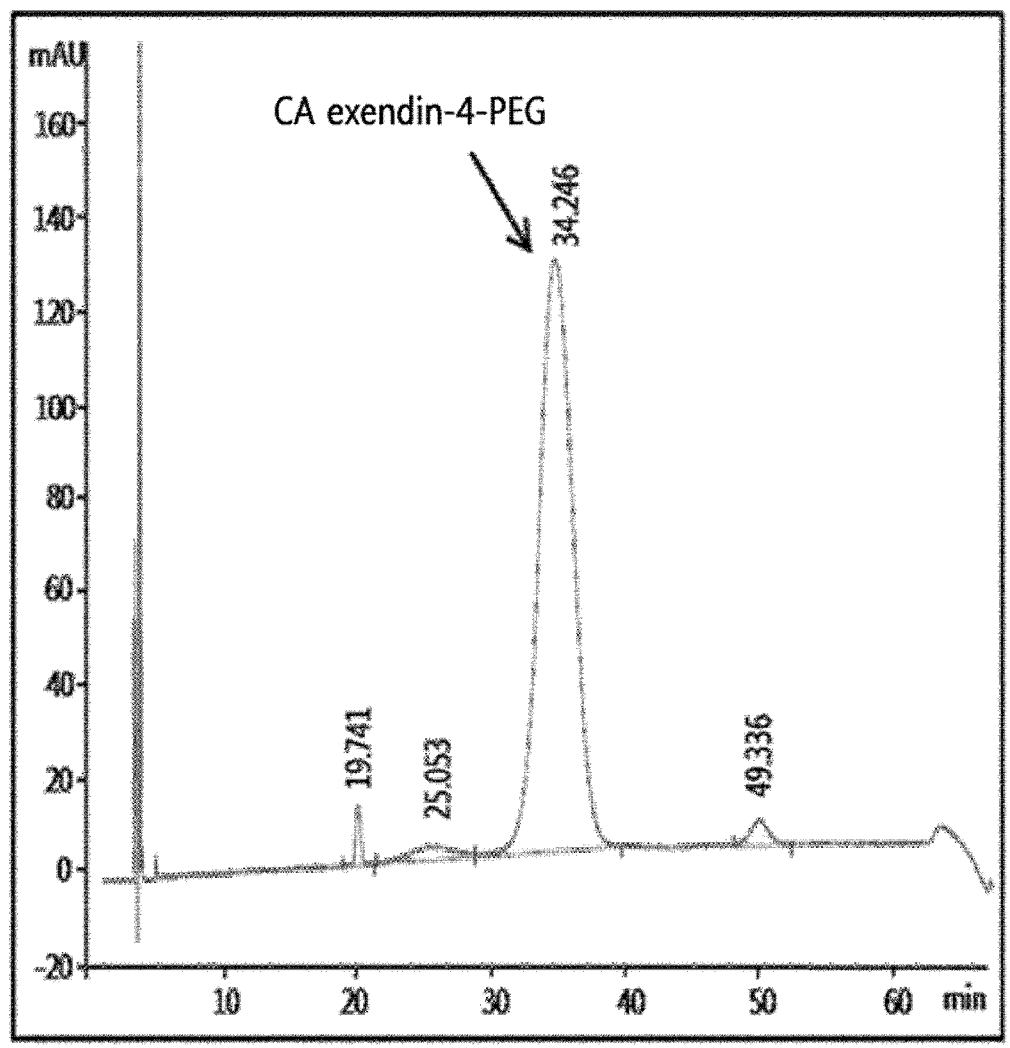

[Fig. 14]
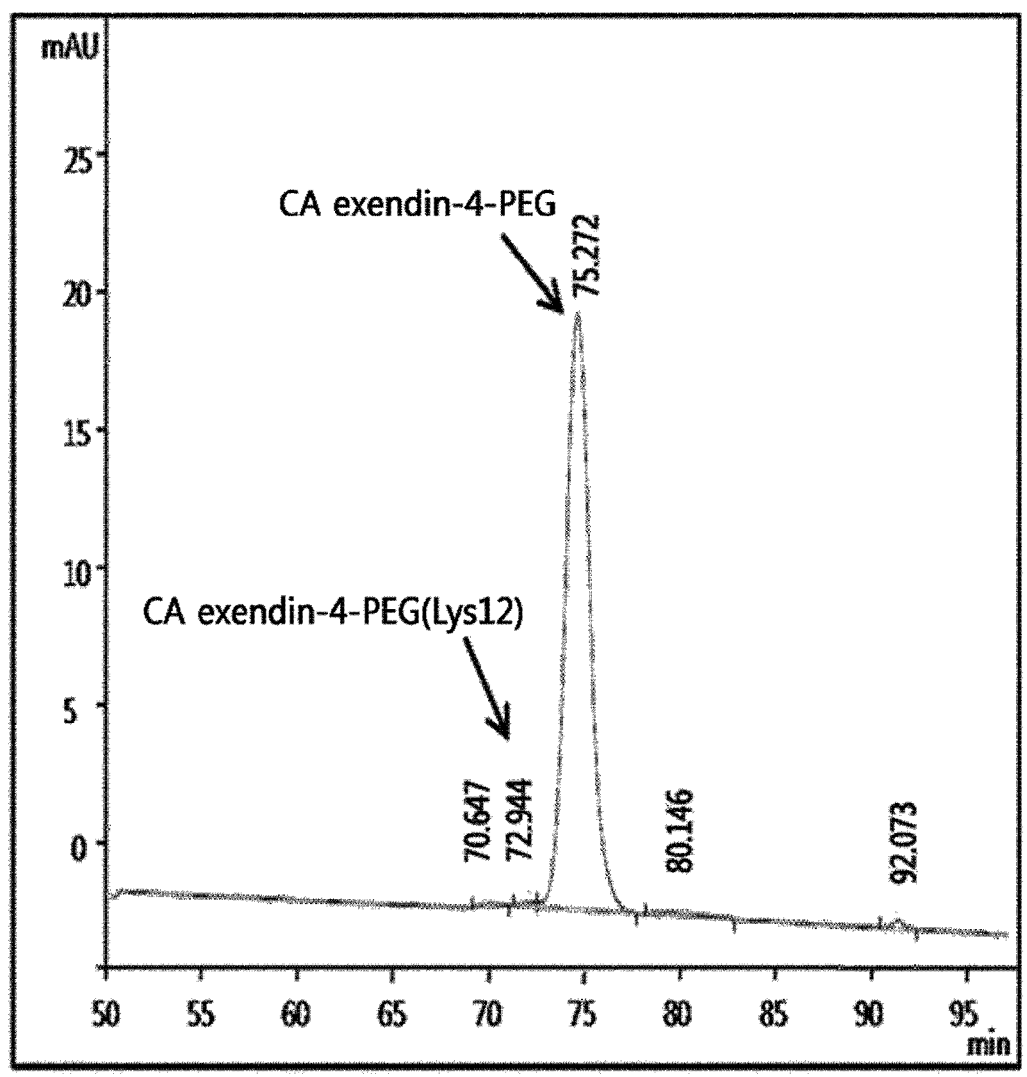

[Fig. 15]
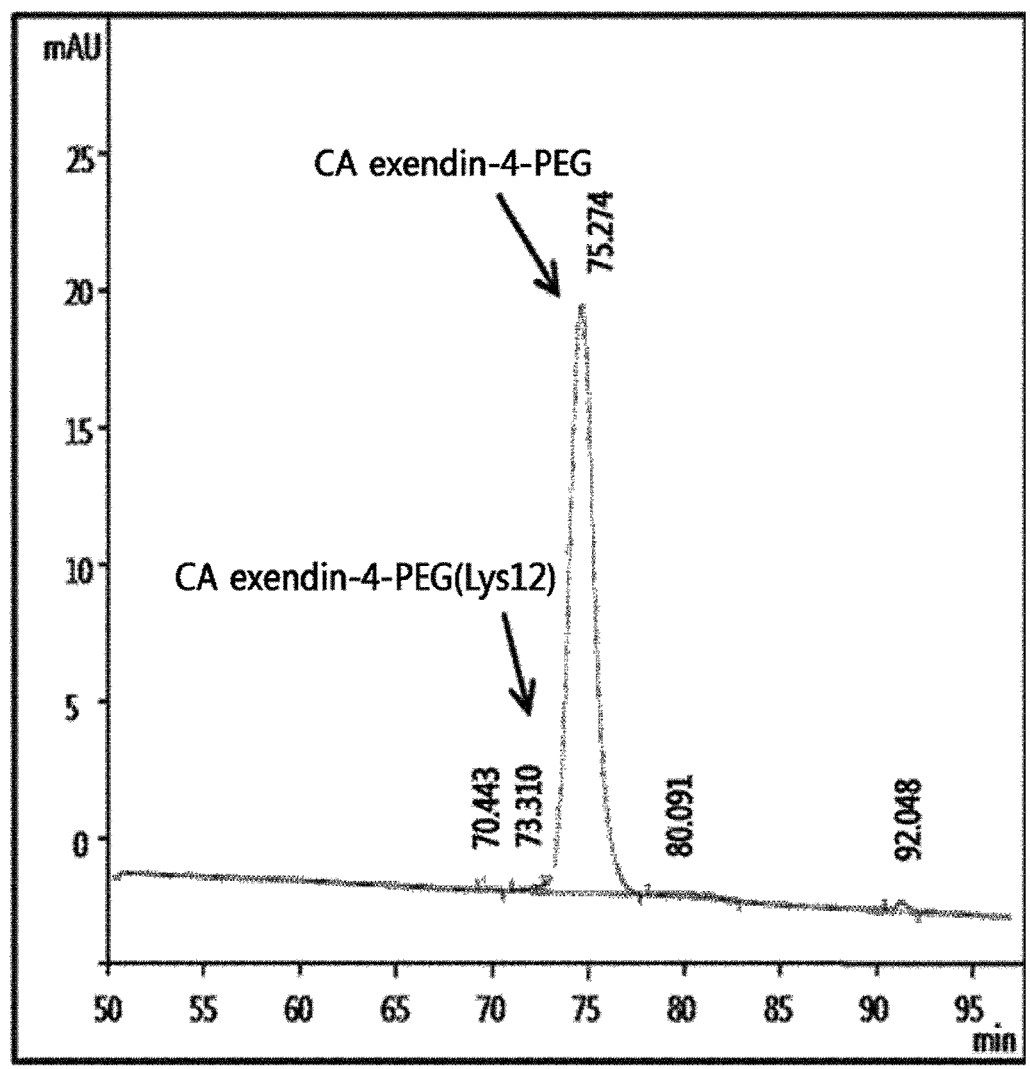

[Fig. 16]
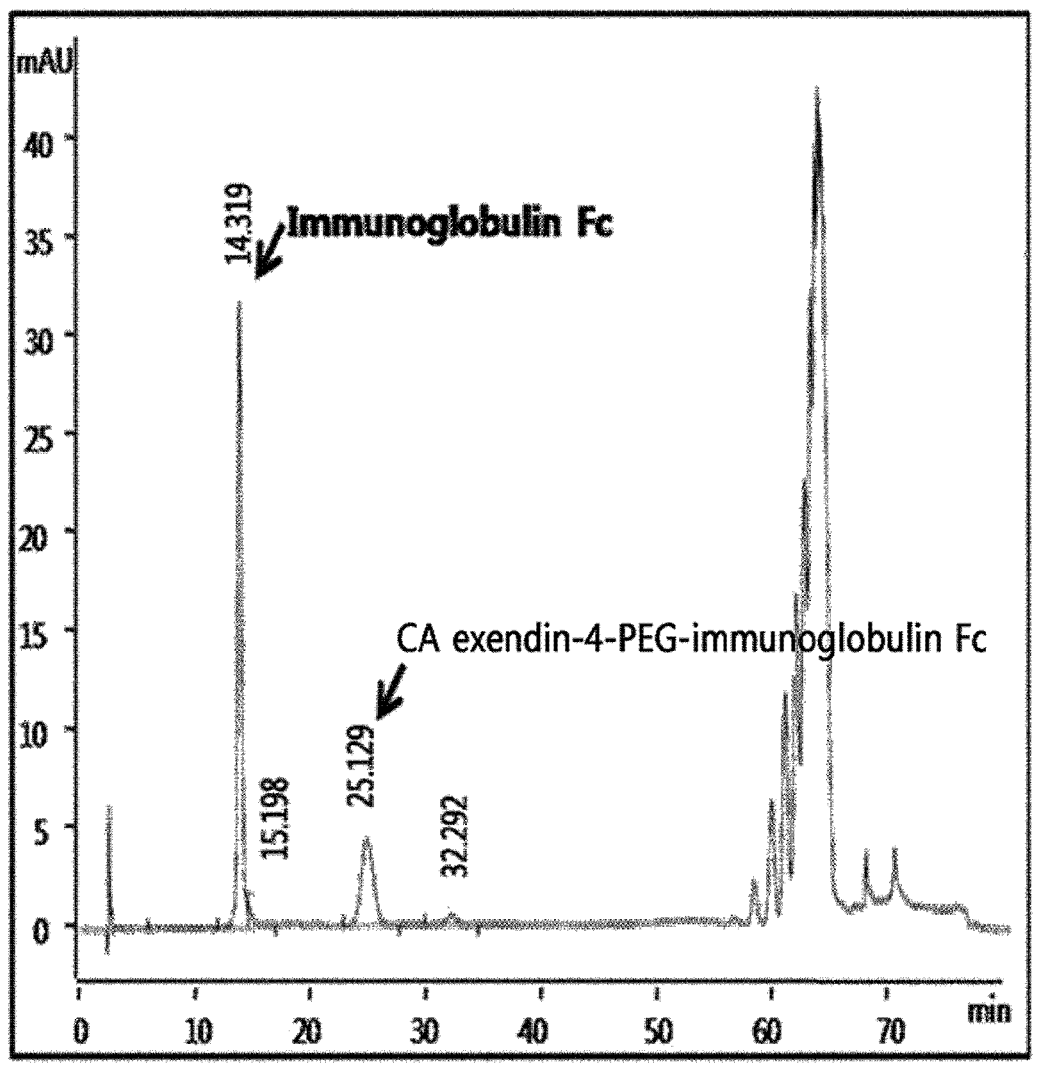

[Fig. 17]
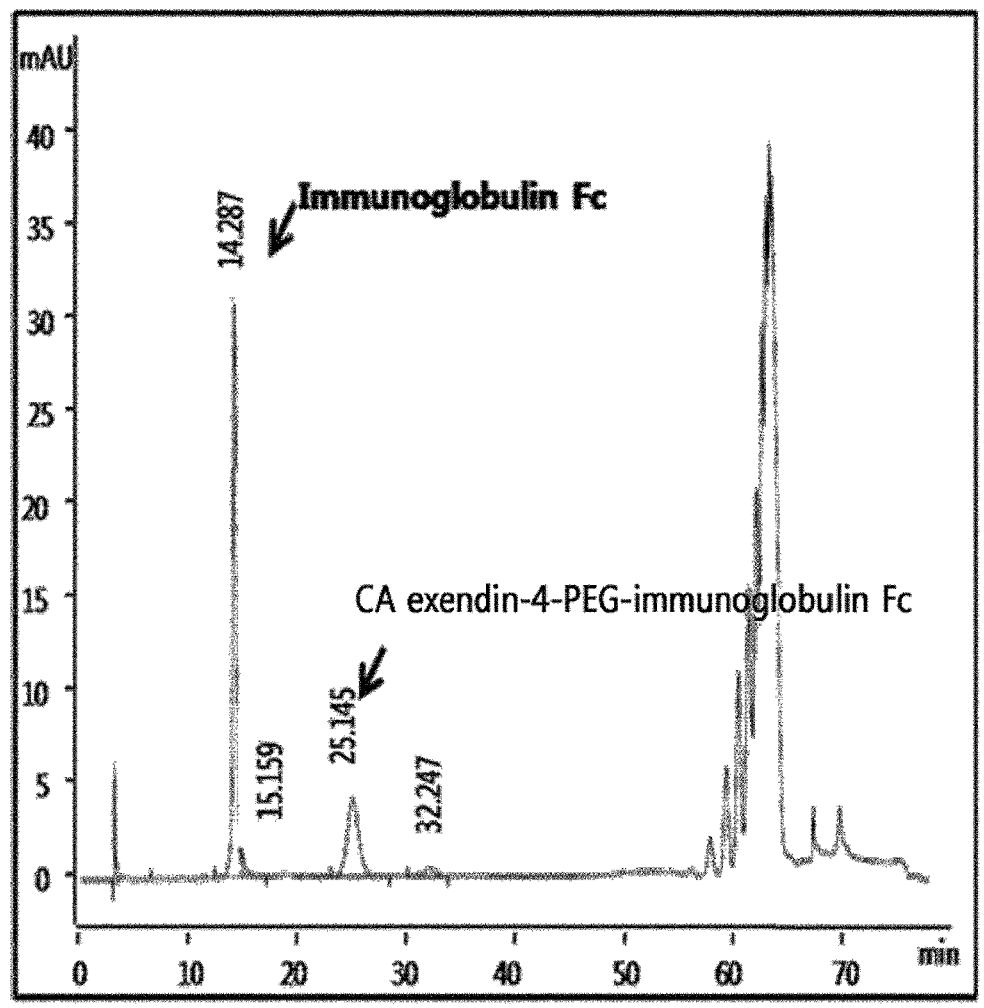
[Fig. 18]
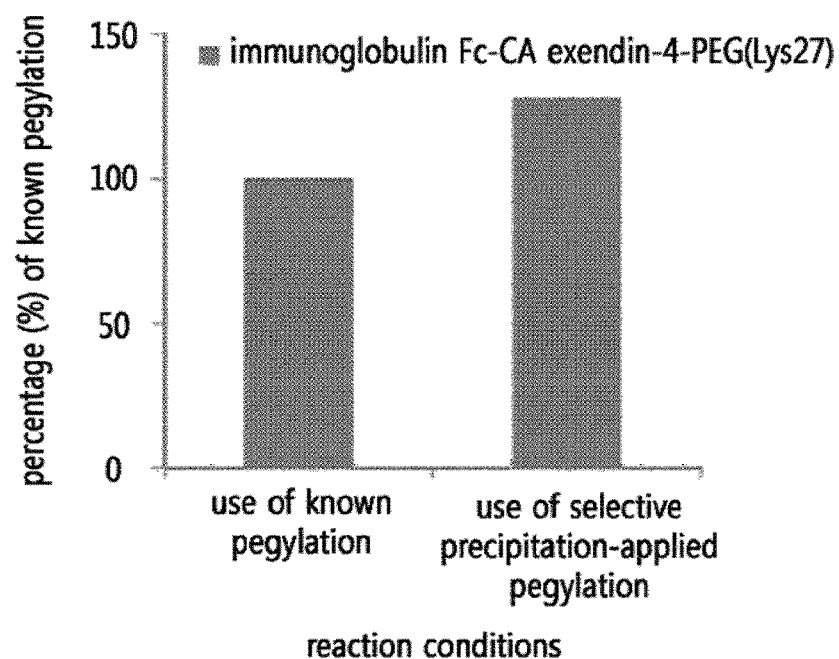

[Fig. 19]
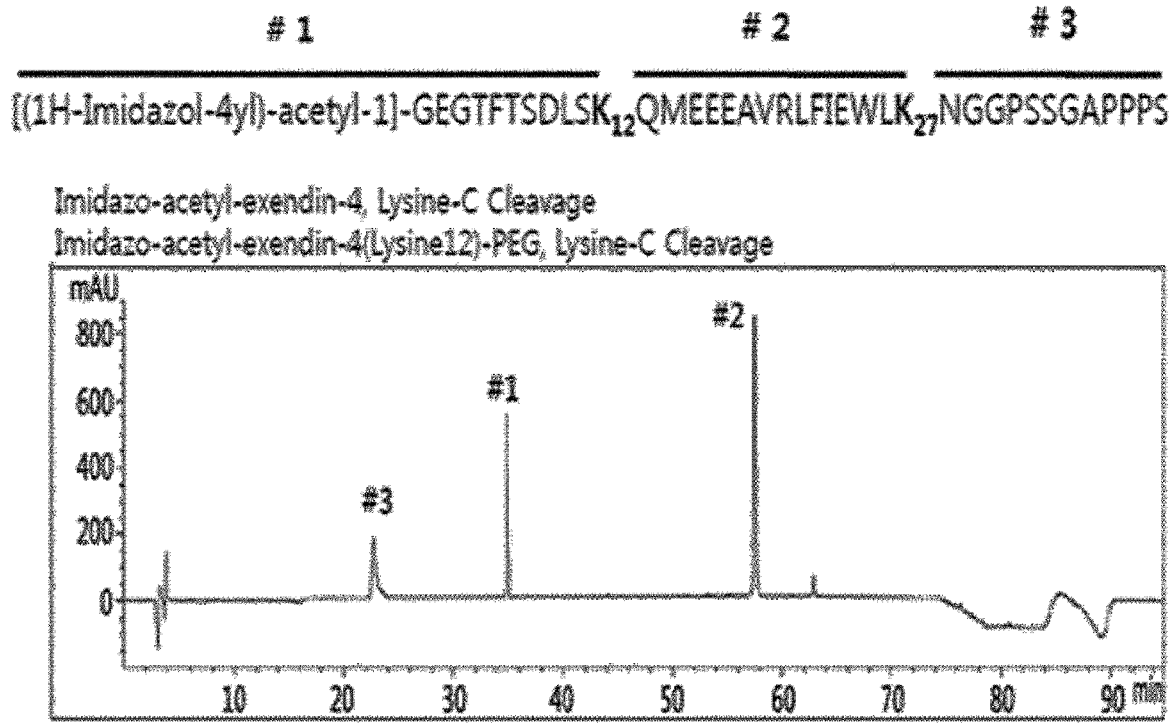
[Fig. 20]
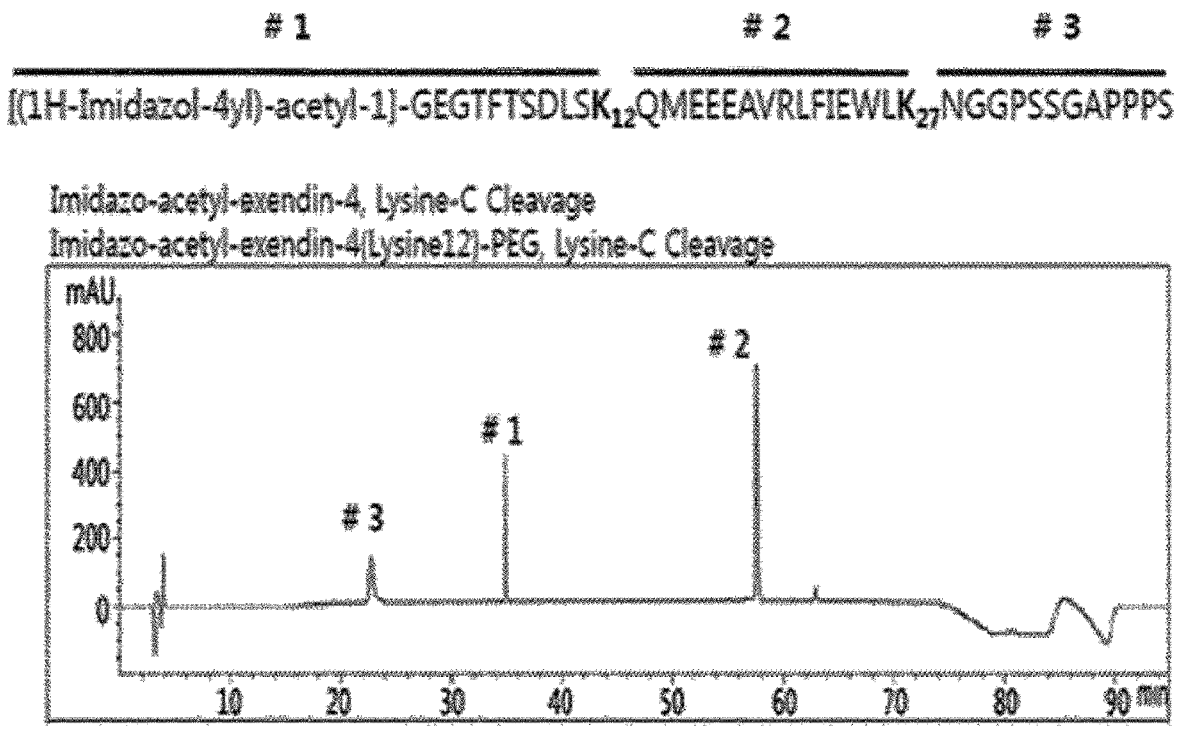

[Fig. 21]
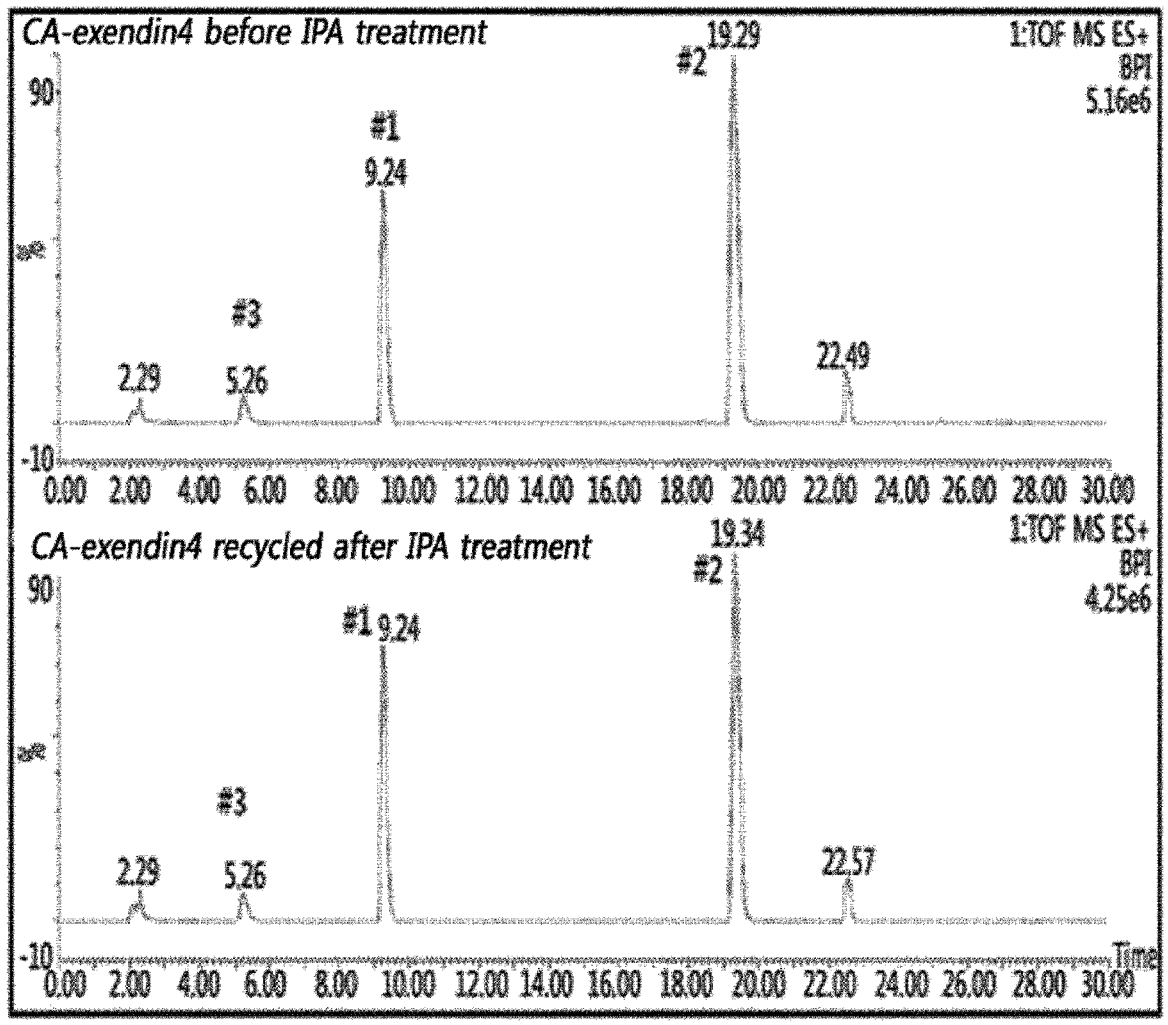
1 : [(1H-Imidazol-4yl)-acetyl-1]-Gly(2)-Lys(12) (exact mass 1248.6)
2 : Gln(13)- Lys(27) (exact mass 1920.0)
3 : Asn(28)-Ser(39)-$NH_2$ (exact mass 1022.5)

[Fig. 22]
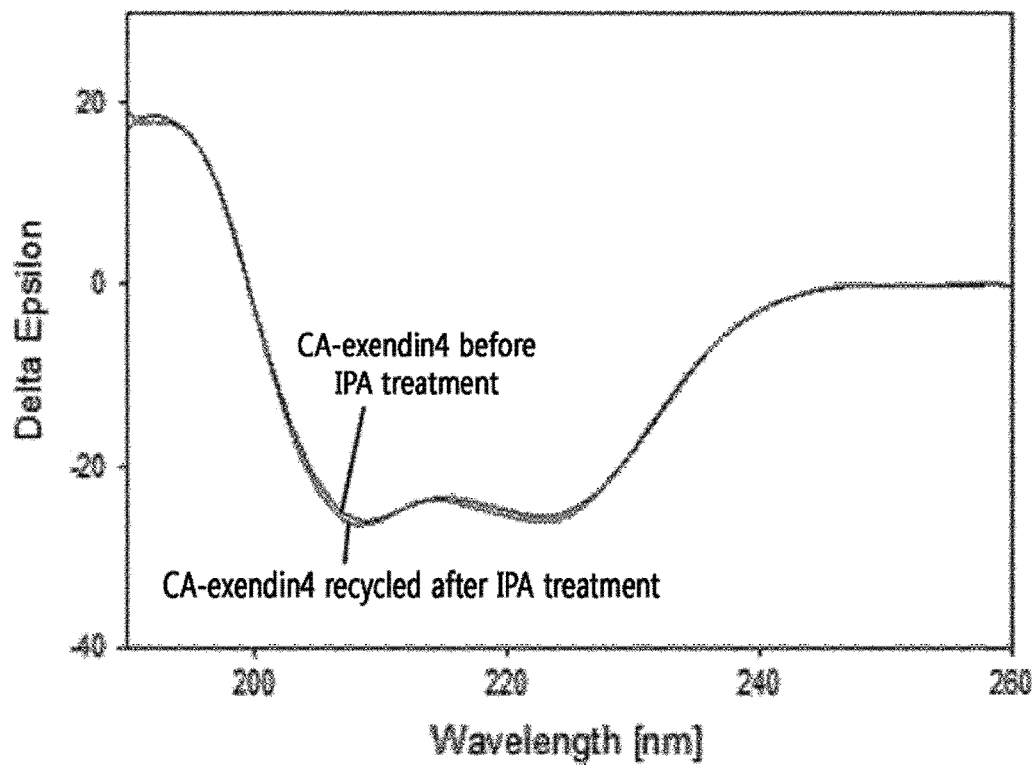
[Fig. 23]
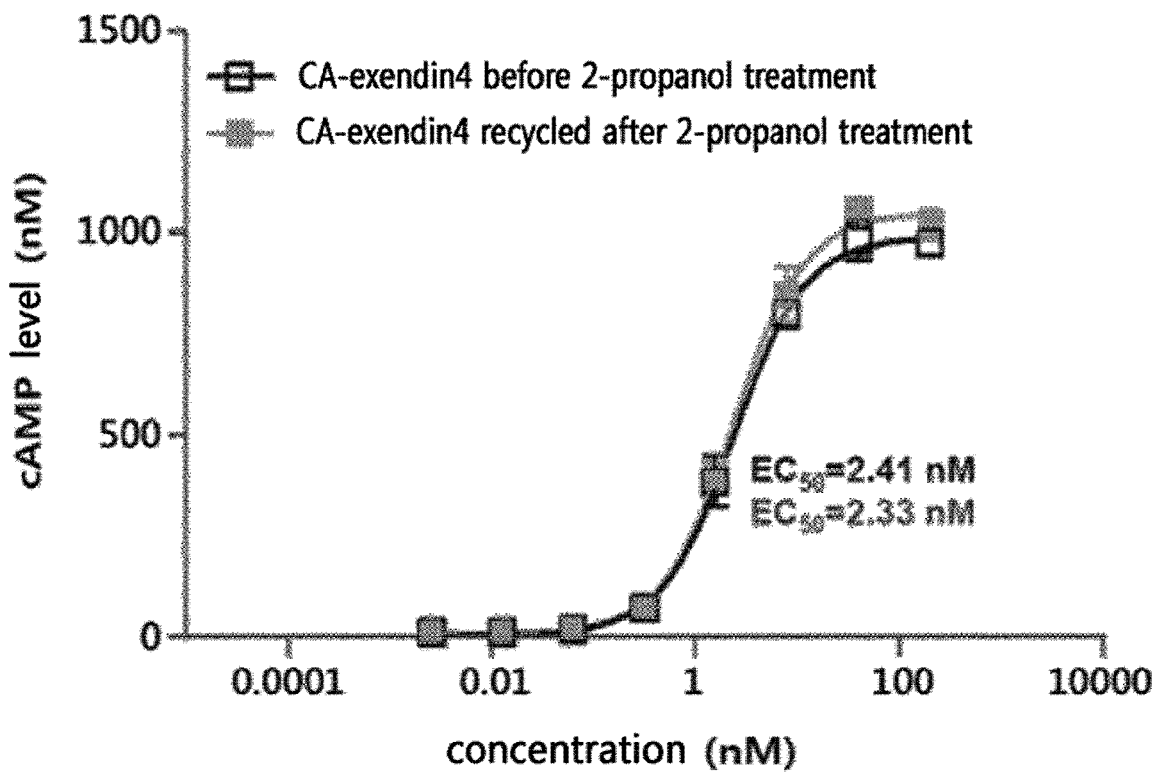

METHOD OF PREPARING PHYSIOLOGICALLY ACTIVE POLYPEPTIDE CONJUGATE

CROSS-REFERENCE TO RELATED APPLICATIONS

This application is a National Phase application under 35 U.S.C. § 371 of International Application No. PCT/KR2016/008050, filed Jul. 22, 2016, which claims priority benefit to KR Application No. 10-2015-0105310, filed Jul. 24, 2015, the disclosures of each of which are herein incorporated by reference in their entirety.

TECHNICAL FIELD

The present invention relates to a method of preparing a physiologically active polypeptide conjugate in which a physiologically active polypeptide and a non-peptidyl polymer are linked to each other via a covalent bond. The method is to improve an overall yield of the physiologically active polypeptide conjugate by improving a reaction of the non-peptidyl polymer and the physiologically active polypeptide, and particularly, the method is to prepare a physiologically active polypeptide conjugate in a high yield by performing a two-step reaction through selective precipitation.

BACKGROUND ART

Peptides tend to be easily denatured due to their low stability and degraded by in vivo proteolytic enzymes, thus losing activity. Peptides have a relatively small size, and thereby easily pass through the kidney. Accordingly, in order to maintain the blood level and potency of a drug including a peptide as a pharmaceutically active component, it is necessary to administer the peptide drug to a patient frequently. However, the peptide drugs are usually administered in the form of injectable preparations, and such frequent administration to maintain the blood levels of the physiologically active peptide causes severe pain for the patients. There have been many attempts to solve these problems, including delivery of a peptide drug into the body through oral or nasal inhalation by increasing the bio membrane permeability of the peptide drug; modification of a particular amino acid sequence sensitive to protease in order to stabilize the peptide and to prevent degradation by protease (for example, modification of a GLP-1 amino acid sequence to prevent loss of potency by dipeptidyl peptidase, etc.); chemical addition of a polymer material having high solubility such as polyethylene glycol (PEG) to the surface of the peptide; and preparation of a fusion protein of a physiologically active polypeptide and human serum albumin or an immunoglobulin fragment (Fc) using a recombinant fusion technology.

However, preparation of the fusion protein is problematic in that non-specific binding of the polymer to the physiologically active peptide blocks active domains of the peptide to reduce activity of the peptide, and thus site-specific binding to prevent the non-specific binding reduces a preparation yield or requires artificial manipulation of the physiologically active peptide.

In order to solve the problem of inefficient preparation of a conjugate of the physiologically active polypeptide and the non-peptidyl polymer, there has been an attempt to modify a specific site of the physiologically active polypeptide in the physiologically active polypeptide conjugate with a non-peptidyl polymer (Korean Patent No. 10-1164453).

Further, in the preparation of a fusion protein of a physiologically active polypeptide and human serum albumin or an immunoglobulin fragment (Fc) by using a non-peptidyl polymer having two functional groups, many methods have been attempted to increase a preparation yield.

The present inventors have continued their studies, and they have found that after a first conjugation reaction between a non-peptidyl polymer and a physiologically active polypeptide, the unreacted (unconjugated) physiologically active polypeptide is separated by selective precipitation, and is then subjected to a second reaction to produce a non-peptidyl polymer-physiologically active polypeptide conjugate in a high yield and high purity, and the conjugate is used to produce a physiologically active polypeptide-physiologically active carrier conjugate in a high yield and high purity, thereby completing the present invention.

DISCLOSURE OF INVENTION

Technical Problem

An object of the present invention is to provide a method of preparing a physiologically active polypeptide conjugate, the method including: 1) selectively precipitating from a reaction mixture a physiologically active polypeptide unconjugated to a non-peptidyl polymer, said reaction conjugating the non-peptidyl polymer to an amino acid residue of the physiologically active polypeptide; and 2) reacting the physiologically active polypeptide recovered from the precipitate with the non-peptidyl polymer under the conjugation reaction of step 1).

Another object of the present invention is to provide a method of preparing a conjugate of a physiologically active polypeptide and a physiologically active carrier, the method comprising conjugating via a covalent bond, the physiologically active polypeptide conjugate prepared as described above with a physiologically active carrier to prepare a polypeptide-carrier conjugate, wherein in the polypeptide-carrier conjugate, the two ends of the non-peptidyl polymer are respectively conjugated to the physiologically active carrier and the physiologically active polypeptide.

Solution to Problem

To achieve the above objects, an aspect of the present invention provides a method of preparing a physiologically active polypeptide conjugate, the method including:

1) selectively precipitating from a reaction mixture a physiologically active polypeptide unconjugated to a non-peptidyl polymer, said reaction conjugating the non-peptidyl polymer to an amino acid residue of the physiologically active polypeptide; and 2) reacting the physiologically active polypeptide recovered from the precipitate with the non-peptidyl polymer under the conjugation reaction of step 1).

A specific embodiment of the present invention provides the preparation method in which the precipitated physiologically active polypeptide is dissolved and then conjugated to the non-peptidyl polymer.

Another specific embodiment of the present invention provides the preparation method in which the reaction mixture in step 1) includes 10% by weight or more based on the total weight of the mixture, of the physiologically active polypeptide to which the non-peptidyl polymer is not bound.

Still another specific embodiment of the present invention provides the preparation method in which the selective precipitation in step 1) is performed using an organic solvent.

Still another specific embodiment of the present invention provides the preparation method in which the organic solvent is isopropanol.

Still another specific embodiment of the present invention provides the preparation method in which the reaction mixture in step 1) is treated with isopropanol in 2 volumes or more of that of the reaction mixture.

Still another specific embodiment of the present invention provides the preparation method in which the reaction mixture in step 1) is treated with isopropanol in 3 to 7 volumes of that of the reaction mixture.

Still another specific embodiment of the present invention provides the preparation method in which, in step 2), the recovered physiologically active polypeptide is reacted with the non-peptidyl polymer for 0.5 hours to 4 hours.

Still another specific embodiment of the present invention provides the preparation method in which the physiologically active polypeptide is selected from the group consisting of insulin-secreting peptide, blood coagulation factor, digestion-promoting hormone, insulin, oxyntomodulin, glucagon, adrenocortical hormone, thyroid hormone, intestinal hormone, cytokines, enzymes, growth factor, neuropeptide, pituitary hormone, hypothalamus hormone, anti-obesity peptide, anti-virus peptide, and a non-natural peptide derivative with physiological activity.

Still another specific embodiment of the present invention provides the preparation method in which the physiologically active polypeptide is selected from the group consisting of erythropoietin, granulocyte-colony stimulating factor, amylin, somatostatin, peptide YY (PYY), neuropeptide Y (NPY), angiotensin, bradykinin, calcitonin, corticotropin, eledoisin, gastrin, leptin, oxytocin, vasopressin, luteinizing hormone, luteotrophic hormone, follicle-stimulating hormone, parathyroid hormone, secretin, sermorelin, human growth hormone (hGH), growth hormone-releasing peptide, granulocyte colony stimulating factors (GCSFs), interferons (IFNs), interleukins, prolactin-releasing peptide, orexia, thyroid-releasing peptide, cholecystokinin, gastrin-inhibiting peptide, calmodulin, gastrin-releasing peptide, motilin, vasoactive intestinal peptide, atrial natriuretic peptide (ANP), barin natriuretic peptide (BNP), C-type natriuretic peptide (CNP), neurokinin A, neuromedin, renin, endothelin, sarafotoxin peptide, carsomorphin peptide, dermorphin, dynorphin, endorphin, enkepalin, T cell factor, tumor necrosis factor, tumor necrosis factor receptor, urokinase receptor, tumor suppressor, collagenase inhibitor, thymopoietin, thymulin, thymopentin, tymosin, thymic humoral factor, adrenomodullin, allatostatin, amyloid beta-protein fragment, antibacterial peptide, antioxidant peptide, bombesin, osteocalcin, CART peptide, E-selectin, ICAM-1, VCAM-1, leucokine, Kringle-5, laminin, inhibin, galanin, fibronectin, pancreastatin, and fuzeon.

Still another specific embodiment of the present invention provides the preparation method in which the physiologically active polypeptide is exendin, insulin, an exendin derivative, an insulin derivative or a combination thereof.

Still another specific embodiment of the present invention provides the preparation method in which the exendin derivative is selected from the group consisting of des-amino-histidyl(DA)-exendin-4, beta-hydroxy-imidazo-propionyl(HY)-exendin-4, imidazo-acetyl(CA)-exendin-4, and dimethyl-histidyl(DM)-exendin-4.

Still another specific embodiment of the present invention provides the preparation method in which the non-peptidyl polymer is conjugated to Lys27 of exendin, which is a physiologically active polypeptide, or a derivative thereof.

Still another specific embodiment of the present invention provides the preparation method in which the non-peptidyl polymer is conjugated to N-terminus of insulin or insulin analog β-chain, which is a physiologically active polypeptide, or a derivative thereof.

Still another specific embodiment of the present invention provides the preparation method in which the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitins, hyaluronic acid, and a combination thereof.

Still another specific embodiment of the present invention provides the preparation method in which the non-peptidyl polymer is polyethylene glycol.

Still another specific embodiment of the present invention provides the preparation method in which the non-peptidyl polymer includes at least one reactive group selected from the group consisting of an aldehyde group, a propionaldehyde group, a butyraldehyde group, a maleimide group, and a succinimide derivative.

Still another specific embodiment of the present invention provides the preparation method in which the non-peptidyl polymer has an aldehyde group as a reactive group.

Still another specific embodiment of the present invention provides the preparation method in which the aldehyde group is a propionaldehyde group.

Still another specific embodiment of the present invention provides the preparation method in which the non-peptidyl polymer has a molecular weight from 500 Da to 100,000 Da.

Still another specific embodiment of the present invention provides the preparation method further including separating the physiologically active polypeptide conjugate after step 2).

Still another specific embodiment of the present invention provides the preparation method in which the separation is performed using ion exchange chromatography.

Still another specific embodiment of the present invention provides the preparation method in which the ion exchange chromatography is high pressure ion exchange chromatography.

Another aspect of the present invention is to provide a method of preparing a conjugate of a physiologically active polypeptide and a physiologically active carrier (physiologically active polypeptide-physiologically active carrier, polypeptide-carrier conjugate). This method includes conjugating by a covalent bond, the physiologically active carrier with the physiologically active polypeptide conjugate prepared as describe above, thereby preparing a conjugate (physiologically active polypeptide-physiologically active carrier, polypeptide-carrier conjugate) in which the two ends of the non-peptidyl polymer are respectively conjugated to the physiologically active carrier and the physiologically active polypeptide.

A specific embodiment of the present invention provides the preparation method in which the physiologically active carrier is selected from the group consisting of albumin, an immunoglobulin Fc region, transferrin, aptamer, toxin, gelatin, collagen, dextran, polysaccharide, fatty acid, and fibrinogen.

Another specific embodiment of the present invention provides the preparation method in which the physiologically active carrier is an immunoglobulin Fc region.

Advantageous Effects of Invention

A preparation method of the present invention is used to produce a non-peptidyl polymer-physiologically active polypeptide conjugate and a physiologically active polypeptide-physiologically active carrier conjugate by a two-step reaction through selective precipitation in a high yield, and therefore, the method may be used in the development of long-acting formulations of various peptide drugs which maintain in vivo activity at a relatively high level and have remarkably increased blood half-life.

BRIEF DESCRIPTION OF DRAWINGS

FIG. 1 is a schematic illustration of the known pegylation and an improved pegylation to which selective precipitation is applied;

FIG. 2 is a purification profile of positional isomers obtained by purifying a pegylation product using a SOURCE S column, in which the pegylation product was prepared by pegylation of imidazo-acetyl-exendin-4 at a concentration of 15 mg/mL for 3 hours;

FIG. 3 is a purification profile of positional isomers obtained by purifying a pegylation product using a SP-HP column, in which the pegylation product was prepared by pegylation of insulin analog at a concentration of 5 mg/mL for 2 hours;

FIG. 4 shows a result of SDS-PAGE analysis of mixtures containing aqueous solutions and precipitates obtained by treatment of a pegylation product with iso-propanol, 1-propanol, 1-butanol, acetone and acetonitrile for selective precipitation, in which the pegylation product was prepared by pegylation of imidazo-acetyl-exendin-4 at a concentration of 15 mg/mL for 3 hours;

FIG. 5 shows a result of SDS-PAGE analysis of mixtures containing aqueous solutions and precipitates obtained by treatment of a pegylation product with iso-propanol, ethanol, 1-propanol, acetone and acetonitrile for selective precipitation, in which the pegylation product was prepared by pegylation of insulin analog at a concentration of 5 mg/mL for 2 hours;

FIG. 6 is a purification profile of positional isomers obtained by purifying an aqueous solution using a SOURCE S (LRC, 15×161 mm, 28 mL, PALL) column, in which the aqueous solution was obtained by removing a precipitate after treatment of a pegylation product with isopropanol, and the pegylation product was obtained by pegylation of imidazo-acetyl-exendin-4 at a concentration of 15 mg/mL for 3 hours;

FIG. 7 is a purification profile of positional isomers obtained by purifying a precipitate pegylation product using a SOURCE S column, in which the precipitate was prepared by treatment of a pegylation product with isopropanol, and the pegylation product was obtained by pegylation of imidazo-acetyl-exendin-4 at a concentration of 15 mg/mL for 3 hours;

FIG. 8 is a purification profile of positional isomers obtained by purifying a pegylation product and a product of pegylation of a precipitate using a SOURCE S column, in which the precipitate was prepared by selective precipitation;

FIG. 9 is a purification profile of positional isomers obtained with a SP-HP (Hitrap, 5 mL×4 each, 20 mL, GE Healthcare) column from an aqueous solution made available by removing a precipitate after treatment of a pegylation product with isopropanol, in which the pegylation product was obtained by pegylating an insulin analog at a concentration of 5 mg/mL for 2 hours;

FIG. 10 is a purification profile of positional isomers obtained by purifying a precipitate pegylation product using a SP-HP column, in which the precipitate was prepared by treatment of a pegylation product with isopropanol, and the pegylation product was obtained by pegylation of insulin analog at a concentration of 5 mg/mL for 2 hours;

FIG. 11 is a graph showing an improved yield of a selective precipitation-applied pegylation method, which was represented as a percentage of the known pegylation method;

FIG. 12 is a result of analyzing purity of an imidazo-acetyl-exendin-4-PEG (CA-exendin-4-PEG) conjugate of Example 1 using a reverse phase column;

FIG. 13 is a result of analyzing purity of an imidazo-acetyl-exendin-4-PEG conjugate of Example 7 using a reverse phase column;

FIG. 14 is an analysis profile of Lys27-pegylated positional isomers of imidazo-acetyl-exendin-4 of Example 1 by peptide mapping;

FIG. 15 is an analysis profile of Lys27-pegylated positional isomers of imidazo-acetyl-exendin-4 of Example 7 by peptide mapping;

FIG. 16 is a result of analyzing purity of the imidazo-acetyl-exendin-4-PEG-immunoglobulin Fc conjugate of Example 1 using a reverse phase column;

FIG. 17 is a result of analyzing purity of the imidazo-acetyl-exendin-4-PEG-immunoglobulin Fc conjugate of Example 7 using a reverse phase column;

FIG. 18 is a graph showing a comparison of yield between an imidazo-acetyl-exendin-4-PEG-immunoglobulin Fc (immunoglobulin Fc-CA-exendin-4-PEG(Lys27)) conjugate prepared by a selective precipitation-applied pegylation method and a conjugate prepared by the known pegylation method;

FIG. 19 shows a result of peptide mapping for examining the status before application of selective precipitation (isopropanol treatment);

FIG. 20 shows a result of peptide mapping for examining the status after application of selective precipitation (isopropanol treatment);

FIG. 21 shows changes in a primary structural sequence of imidazo-acetyl-exendin-4 before and after application of selective precipitation (isopropanol treatment) (IPA: isopropanol);

FIG. 22 shows changes in a secondary structure of imidazo-acetyl-exendin-4 before and after application of selective precipitation (isopropanol treatment) (IPA: iso-propanol); and FIG. 23 shows a result of measuring in vivo activity of imidazo-acetyl-exendin-4 before and after application of selective precipitation (isopropanol treatment) (IPA: isopropanol) by a cAMP experiment.

BEST MODE FOR CARRYING OUT THE INVENTION

An aspect of the present invention provides a method of preparing a physiologically active polypeptide conjugate, the method including:

1) selectively precipitating from a reaction mixture a physiologically active polypeptide unconjugated to a non-peptidyl polymer, said reaction conjugating the non-peptidyl polymer to an amino acid residue of the physiologically active polypeptide; and 2) reacting the physiologically active polypeptide recovered from the precipitate with the non-peptidyl polymer under the conjugation reaction of step 1).

As used herein, the term "physiologically active polypeptide conjugate" refers to a material in which a physiologically active polypeptide is covalently linked to one end of a non-peptidyl polymer. In the present invention, the physiologically active polypeptide conjugate is used interchangeably with a non-peptidyl polymer-physiologically active polypeptide conjugate.

Step 1) of the present invention is characterized by selectively precipitating the physiologically active polypeptide to which the non-peptidyl polymer is not bound from the (first) conjugation reaction mixture. This (first) conjugation reaction conjugates the non-peptidyl polymer to the physiologically active polypeptide, preferably selectively, and more preferably site-specifically.

In the present invention, the "physiologically active polypeptide to which the non-peptidyl polymer is not bound" is used interchangeably with "unreacted physiologically active polypeptide" or "unconjugated physiologically active polypeptide".

As used herein, the term "site-specific" means that the non-peptidyl polymer is specifically bonded to a desired amino acid position, in particular, to an amine of a lysine residue or the N-terminal residue among the amino acid positions of the physiologically active polypeptide. When the non-peptidyl polymer is site-specifically linked, the long-acting formulation to be prepared in which the physiological activity is maximized, can be protected from reduction in physiological activity attributable to the presence of other, less desirable conjugates, for example, those in which the non-peptidyl polymer is bonded to an amino acid residue important for physiological activity. For example, in the case of exendin-4, when the non-peptidyl polymer is bonded to the N-terminus of the physiologically active polypeptide, in vitro activity is reduced. In contrast, when the non-peptidyl polymer is bonded to a lysine residue thereof, in vitro activity is maintained. In particular, of the lysine residues at positions 12 and 27 of exendin-4, the resultant conjugate shows higher in vitro activity when the non-peptidyl polymer is bonded to the lysine residue at position 27.

Therefore, in an embodiment of the present invention wherein the physiologically active polypeptide is exendin or an exendin derivative, the non-peptidyl polymer may site-specifically be bonded to lysine at position 12 or 27, in particular, lysine at position 27 of the exendin or an exendin derivative, but the present invention is not limited thereto. The pegylation method of exendin is described in detail in Korean Patent Publication No. 10-2010-0105494, which is incorporated herein by reference.

As used herein, the term "selective precipitation" means that the non-peptidyl polymer-physiologically active polypeptide conjugate resulting from a conjugation reaction of a mixture of the non-peptidyl polymer and the physiologically active polypeptide remains in an aqueous solution, but unreacted physiologically active polypeptide is selectively precipitated.

In the present invention, the selective precipitation may be any method without limitation, as long as it is able to precipitate unreacted physiologically active polypeptide in the reaction mixture. For the purpose of illustration, some examples of widely known precipitation methods of polypeptides are as follows:

1. Salting out,
2. Isoionic precipitation,
3. Two-carbon (C2) organic cosolvent precipitation,
4. C4 and C5, organic cosolvent precipitation, phase partitioning, and extraction of polypeptide,
5. Polypeptide exclusion and crowding agents (neutral polymers) and osmolytes,
6. Synthetic and semisynthetic polyelectrolyte precipitation,
7. Metallic and polyphenolic heteropolyanion precipitation,
8. Hydrophobic ion pairing (HIP) entanglement ligands,
9. Matrix-stacking-ligand coprecipitation,
10. Di- and trivalent metal cation precipitation.

The selective precipitation may use each of the listed methods or suitable combinations thereof.

Specifically, unreacted physiologically active polypeptide may be selectively precipitate d by adding an organic solvent to the reaction mixture, but is not limited thereto. Further, the organic solvent may be, specifically, alcohol, ketone, nitrile or a combination thereof, and more specifically, ethanol, isopropanol, 1-propanol, 1-butanol, acetone, acetonitrile, or a combination thereof, but is not limited thereto. Further, the reaction mixture may be treated with the organic solvent in 2 volumes or more, specifically, 2 to 7 volumes, more specifically, 3 to 7, 4 to 7, or 5 to 7 volumes, and much more specifically 3 to 7 volumes of that of the reaction mixture for selective precipitation of unreacted physiologically active polypeptide, but is not limited thereto.

In the present invention, the reaction mixture used for selective precipitation may include, based on the total weight of the reaction mixture, 10% by weight or more, specifically 20% by weight or more of unreacted or unconjugated physiologically active polypeptide, but is not limited thereto.

As used herein, the term "physiologically active peptide" refers to a material which is intended to exhibit a physiological activity in the human body. In the present invention, the physiologically active peptide may be any peptide which is able to exhibit a physiological activity. For example, the physiologically active peptide may be selected from the group consisting of insulin-secreting peptide, blood coagulation factor, digestion-promoting hormone, glucagon, insulin, oxyntomodulin, adrenocortical hormone, thyroid hormone, intestinal hormone, cytokines, enzymes, growth factor, neuropeptide, pituitary hormone, hypothalamus hormone, anti-obesity peptide, anti-virus peptide, and a non-natural peptide derivative with physiological activity, but is not limited thereto.

Further, the physiologically active peptide may be selected from the group consisting of erythropoietin, granulocyte-colony stimulating factor, amylin, somatostatin, peptide YY (PYY), neuropeptide Y (NPY), angiotensin, bradykinin, calcitonin, corticotropin, eledoisin, gastrin, leptin, oxytocin, vasopres sin, luteinizing hormone, luteotrophic hormone, follicle-stimulating hormone, parathyroid hormone, secretin, sermorelin, human growth hormone (hGH), growth hormone-releasing peptide, granulocyte colony stimulating factors (GCSFs), interferons (IFNs), interleukins, prolactin-releasing peptide, orexin, thyroid-releasing peptide, cholecystokinin, gastrin-inhibiting peptide, calmodulin, gastrin-releasing peptide, motilin, vasoactive intestinal peptide, atrial natriuretic peptide (ANP), barin natriuretic peptide (BNP), C-type natriuretic peptide (CNP), neurokinin A, neuromedin, renin, endothelin, sarafotoxin peptide, carsomorphin peptide, dermorphin, dynorphin, endorphin, enkepalin, T cell factor, tumor necrosis factor, tumor necrosis factor receptor, urokinase receptor, tumor suppressor, collagenase inhibitor, thymopoietin, thymulin, thymopentin, tymosin, thymic humoral factor, adrenomodullin, allatostatin, amyloid beta-protein fragment, antibacterial peptide, antioxidant peptide, bombesin, osteocalcin, CART peptide, E-selectin, ICAM-1, VCAM-1, leucokine, Kringle-5, laminin, inhibin, galanin, fibronectin, pancreastatin, and fuzeon, but is not limited thereto.

The physiologically active polypeptide may also include precursors, derivatives, fragments, and variants of the polypeptide, which have the physiological activity of the polypeptide.

Further, the physiologically active polypeptide may be specifically exendin, GLP-1, insulin, oxyntomodulin, glucagon, and derivatives thereof, or calcitonin, but is not limited thereto. In the present invention, the exendin derivatives may be prepared, e.g., by chemical substitution (e.g., alpha-methylation or alpha-hydroxylation), deletion (e.g., deamination), or modification (e.g., N-methylation) of any groups on an amino acid residue, or combination thereof, and the exendin derivative is described in detail in Korean Patent Publication No. 10-2009-0008151. Further, the exendin derivative may be specifically selected from the group consisting of des-amino-histidyl(DA)-exendin-4, beta-hydroxy-imidazo-propionyl(HY)-exendin-4, imidazo-acetyl (CA)-exendin-4, and dimethyl-histidyl(DM)-exendin-4, but is not limited thereto.

As used herein, the term "non-peptidyl polymer" refers to a biocompatible polymer including one or more repeating units linked to each other by a covalent bond excluding a peptide bond.

The non-peptidyl polymer which can be used in the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid)), PVP (polyvinylpyrrolidone), and PLGA (polylactic-glycolic acid), lipid polymers, chitins, hyaluronic acid, and combinations thereof, and specifically, polyethylene glycol, but is not limited thereto. Also, derivatives thereof well known in the art and which are easily prepared within the skill of the art are included in the scope of the present invention.

Any non-peptidyl polymer may be used without limitation, as long as it is a polymer that has a resistance to in vivo proteolytic enzymes, and thus is not easily cleaved by proteolytic enzymes to allow the physiologically active polypeptide to exhibit a sufficient activity. The non-peptidyl polymer has a molecular weight in the range of 0.5 kDa to 100 kDa, and specifically, of 0.5 kDa to 20 kDa. Also, the non-peptidyl polymer of the present invention, linked to the physiologically active polypeptide, may be one polymer or a combination of different types of polymers.

Further, the non-peptidyl polymer used in the present invention may have a reactive group at one end thereof or at both ends thereof. The non-peptidyl polymer having a reactive group at both ends thereof may bind to a physiologically active carrier and a protein drug which assist in functioning as a long acting formulation.

Specifically, the non-peptidyl polymer has a reactive group at both ends which is selected from the group consisting of an aldehyde group, a propionaldehyde group, a butyraldehyde group, a maleimide group, and a succinimide derivative, more specifically, the aldehyde group, and much more specifically, the propionaldehyde group, but is not limited thereto. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends, it is effective in linking at both ends with a physiologically active polypeptide and a physiologically active carrier with minimal non-specific reactions. A final product generated by reductive alkylation by an aldehyde bond is much more stable than when linked by an amide bond. The aldehyde reactive group selectively binds to an amino N-terminus at a low pH, for example, at a pH of 2.0 to 7.0, specifically, at a pH of 3.0 to 6.0, and more specifically, at a pH of 4.0 to 6.0. Also the aldehyde reactive group may bind to a lysine residue to form a covalent bond at a high pH, for example, at a pH of 6.5 to 9.0, specifically, at a pH of 6.5 to 8.0, and more specifically, at a pH of 6.5 to 7.5.

In the present invention, the reactive groups at both ends of the non-peptidyl polymer may be the same as or different from each other. When a polyethylene glycol having a reactive hydroxyl group at both ends thereof is used as the non-peptidyl polymer, the hydroxyl group may be activated into various reactive groups by known chemical reactions, or a commercially available polyethylene glycol having a modified reactive group may be used.

In a specific example of the present invention, the non-peptidyl polymer is polyethylene glycol with aldehyde end groups and the conjugation reaction of step 1) is site-specific pegylation. This site-specific pegylation may be performed by art-known methods, for example, reductive amination to an amino group such as the E-amino group of lysine or the N-terminus of the physiologically active polypeptide.

As used herein, the term "physiologically active polypeptide conjugate" refers to a material in which a physiologically active polypeptide is covalently linked to one end of a non-peptidyl polymer. In the present invention, the physiologically active polypeptide conjugate is used interchangeably with a non-peptidyl polymer-physiologically active polypeptide conjugate.

Further, in the reaction of the physiologically active polypeptide and the non-peptidyl polymer of the present invention, a reaction molar ratio is not limited, as long as the physiologically active polypeptide and the non-peptidyl polymer form a covalent bond, and the reaction molar ratio of physiologically active polypeptide:non-peptidyl polymer may be properly within the range from 1:1 to 1:30.

Further, in the reaction of the physiologically active polypeptide and the non-peptidyl polymer of the present invention, a reaction time is not limited, as long as the physiologically active polypeptide and the non-peptidyl polymer form a covalent bond, and the reaction time may be, specifically, 0.5 hours to 4.0 hours, and more specifically, 0.5 hours to 2.0 hours, but is not limited thereto.

Further, in the reaction of the physiologically active polypeptide and the non-peptidyl polymer of the present invention, the reaction temperature is not limited, as long as the physiologically active polypeptide and the non-peptidyl polymer form a covalent bond, and the reaction temperature may be, specifically, 0° C. to 14° C. or 15° C. to 30° C., and more specifically, 4° C. to 8° C. or 20° C. to 25° C., but is not limited thereto.

Further, in the reaction of the physiologically active polypeptide and the non-peptidyl polymer of the present invention, a concentration of the physiologically active polypeptide is not limited, as long as the physiologically active polypeptide and the non-peptidyl polymer form a covalent bond, and the concentration may be, specifically, 1 mg/mL to 25 mg/mL, and more specifically, 5 mg/mL to 18 mg/mL, but is not limited thereto.

In an embodiment, the present invention provides the method for preparing a physiologically active polypeptide conjugate in which a modified exendin-4 is linked to polyethylene glycol (PEG). In a more specific embodiment of the present invention, this modified exendin-4 is imidazo-acetyl-exendin-4 (CA-exendin-4) and it can be pegylated at its Lys position using a 3.4 kDa polyethylene glycol with aldehyde functionality at both ends (e.g., 3.4K ALD(2) PEG) at a molar ratio of the peptide and PEG of about 1:7.5 and a peptide concentration of about 5 mg/mL to 18 mg/mL for 0.5 hours to 4.0 hours at 4° C. to 8° C. and 20° C. to 25° C. in a 100 mM HEPES buffer solution at a pH of 6.5 to 7.5 containing 20 mM sodium cyanoborohydride(SCB, $NaCNBH_3$) as a reducing agent. Specifically, 15 mg/mL of the peptide can be reacted for 3 hours at 4° C. to 8° C., and then imidazo-acetyl exendin-4-PEG can be separated from each reaction mixture using a SOURCE 15S column with a linear concentration gradient of KCl in a citric acid buffer solution at pH 2.0. For example, the inventors were able to confirm that such reaction mixture includes about 10% to 40% of $(PEG)_n$-imidazo-acetyl exendin-4+imidazo-acetyl exendin-4-PEG(Lys12), 40% to 50% of imidazo-acetyl exendin-4-PEG, and about 20% to 50% of unreacted imidazo-acetyl exendin-4 (Tables 1 and 2).

In another embodiment, the present invention provides the method for preparing a physiologically active polypeptide conjugate in which an insulin analog is linked to polyethylene glycol (PEG). The insulin analog can be pegylated at the N-terminus of its β-chain using 3.4K ALD(2) PEG at a molar ratio of the peptide and PEG of about 1:4 and a peptide concentration of about 5 mg/mL to 18 mg/mL for 0.5 hours to 4.0 hours at 4° C. to 8° C. and 20° C. to 25° C. in a 50 mM Sodium citrate buffer solution at a pH of 4.0 to 6.0 containing 3-5 mM SCB ($NaCNBH_3$) as a reducing agent. Specifically, 5 mg/mL of the peptide can be reacted for 2 hours at 4° C. to 8° C., and then insulin analog can be separated from each reaction mixture using a SP-HP column with a linear concentration gradient of KCl in a citric acid buffer solution at pH 3.0. For example, the inventors were able to confirm that such reaction mixture includes about 10% to 20% of $(PEG)_n$-insulin analog, 50% to 60% of insulin analog-PEG, and about 5% to 20% of unreacted insulin analog.

In a further specific embodiment of the present invention, the reaction mixture for the pegylated conjugate of either CA-exendin-4 or the insulin analog above is reacted with 2 or more volumes of isopropanol, specifically, 3 to 7 volumes (to that of the reaction mixture). This isopropanol-treated reaction mixture is then separated into an aqueous solution comprising the pegylated conjugate (of either imidazo-acetyl-exendin-4 or the insulin analog) and a precipitate of the unconjugated physiologically active polypeptide, i.e., non-pegylated, unreacted imidazo-acetyl-exendin-4 or unreacted insulin analog (FIGS. 4 and 5). For example, the aqueous solution was purified (FIGS. 6 and 9), and as a result, the inventors were able to confirm that the aqueous solution includes about 10% to 40% of $(PEG)_n$-imidazo-acetyl exendin-4+imidazo-acetyl exendin-4-PEG(Lys12), about 40% to 50% of imidazo-acetyl exendin-4-PEG, and about 5% to 15% of unreacted imidazo-acetyl exendin-4. In case of insulin analog, the aqueous solution includes about 10% to 20% of $(PEG)_n$-insulin analog, 50% to 60% of insulin analog-PEG, and about 5% to 15% of unreacted insulin analog.

The content of the separated imidazo-acetyl-exendin-4 precipitate is 15% to 30% (Table 3).

In a specific embodiment of the present invention, change of imidazo-acetyl exendin-4 was observed before and after treatment with isopropanol. As a result, there was no change in all aspects before and after treatment with isopropanol (FIGS. 19 and 20), and there were no changes in the primary structure (FIG. 21), the content of a secondary structure (FIG. 22 and Table 7), and the activity (FIG. 23 and Table 8). These results indicate that selective precipitation by treatment with isopropanol causes no adverse effect on the physiologically active polypeptide imidazo-acetyl exendin-4.

In the present invention, imidazo-acetyl-exendin-4-PEG is used interchangeably with imidazo-acetyl-exendin-4-PEG (Lys27), imidazo-acetyl exendin-4(Lys27)-PEG, CA-exendin-4-PEG, and CA-exendin-4-PEG(Lys27).

Step 2) of the present invention is characterized in that a second reaction mixture conjugats the physiologically active polypeptide and the non-peptidyl polymer to prepare a non-peptidyl polymer-physiologically active polypeptide conjugate using the physiologically active polypeptide recovered from the precipitate in step 1). Specifically, the precipitated physiologically active polypeptide may be dissolved, and then conjugated to the non-peptidyl polymer preferably selectively, more preferably site-specifically, but is not limited thereto. The aqueous solutions prepared by applying the selective precipitation to the secondary reaction mixture and the first reaction mixture include the prepared non-peptidyl polymer-physiologically active polypeptide conjugate.

In the present invention, reaction conditions of the precipitated physiologically active polypeptide and non-peptidyl polymer are not limited, as long as they are able to form a covalent form, and specifically, the reaction may be performed under the reaction conditions of step 1).

In particular, reaction time of the precipitated physiologically active polypeptide and non-peptidyl polymer may be specifically, 0.5 hours to 4.0 hours, and more specifically, 0.5 hours to 2.0 hours, but is not limited thereto.

In a specific embodiment of the present invention, about 20% to 30% of an imidazo-acetyl-exendin-4 precipitate separated through selective precipitation by treatment with isopropanol in Example 3 was recycled to perform pegylation. As a result, when a re-pegylation solution of the non-pegylated imidazo-acetyl exendin-4 precipitate was purified, about 15% to 40% of $(PEG)_n$-imidazo-acetyl exendin-4+imidazo-acetyl exendin-4-PEG(Lys12), 40% to 50% of imidazo-acetyl exendin-4-PEG, and about 10% to 40% of unreacted imidazo-acetyl exendin-4 were included in the reaction solution (FIG. 7).

The preparation method of the present invention may further include separating the physiologically active polypeptide conjugate after step 2). This procedure may be performed using various separation methods such as chromatography known in the art. Specifically, ion exchange chromatography, and more specifically, high pressure ion exchange chromatography may be used, but it is not limited thereto.

In the present invention, the physiologically active polypeptide conjugate may be separated from the first reaction mixture, the aqueous solution prepared by applying selective precipitation to the first reaction mixture, the second reaction mixture, or combinations thereof.

In particular, when the physiologically active polypeptide conjugate is separated from a mixture of the aqueous solution prepared by applying selective precipitation to the first reaction mixture and the secondary reaction mixture prepared by using the prepcipitate d physiologically active polypeptide, a yield of the physiologically active polypeptide conjugate is remarkably increased compared to separation from the first reaction mixture.

In a specific embodiment of the present invention, the aqueous solution prepared by applying selective precipitation to the first reaction mixture was mixed with the second reaction mixture prepared by re-dissolving the precipitate containing unreacted imidazo-acetyl exendin-4 or insulin analog to perform pegylation, and then separation was performed using a SOURCE 15S column or a SP-HP column with a linear concentration gradient of KCl in citric acid buffer at pH 2.0~pH 3.0. As a result, the yield of the conjugate prepared by the selective precipitation-applied pegylation method was much higher than that of the known pegylation method (FIG. 11 and Table 4).

In a specific embodiment of the present invention, imidazo-acetyl exendin-4 had purity of 97% by both the known pegylation method and the pegylation method to which selective precipitation using isopropanol is applied, and the pegylated positional isomers had similar purity (Table 5).

Further, another aspect of the present invention provides a method of preparing a physiologically active polypeptide-physiologically active carrier conjugate, the method including preparing a conjugate in which both ends of the non-peptidyl polymer are respectively conjugated to the physiologically active carrier and the physiologically active polypeptide by connecting the non-peptidyl polymer and the physiologically active carrier by a covalent bond in the physiologically active polypeptide conjugates prepared by the above preparation method of the physiologically active polypeptide conjugate.

In a specific embodiment of the present invention, the physiologically active polypeptide conjugate prepared by a two-step site-specific pegylation through selective precipitation produces a physiologically active polypeptide-physiologically active carrier conjugate (polypeptide-carrier conjugate) in a high yield and high purity. Such physiologically active polypeptide-physiologically active carrier conjugates show completely different activities compared to the physiologically active polypeptide conjugates from which they derive, i.e., the outstanding physiological activities such as excellent prolonged duration of pharmacological effects of the physiologically active polypeptide, targeting to a specific site such as a lesion to be treated, or induction of necrosis.

In the present invention, the non-peptidyl polymer in the physiologically active polypeptide-physiologically active carrier conjugate should be a non-peptidyl polymer having two ends in order to bind to the physiologically active polypeptide and the physiologically active carrier. That is, the physiologically active carrier may be covalently linked to the end of the non-peptidyl polymer to which the physiologically active polypeptide conjugate does not bond. As a result, a physiologically active polypeptide-physiologically active carrier conjugate in which both ends of the non-peptidyl polymer are respectively linked to the physiologically active polypeptide and the physiologically active carrier is prepared.

As used herein, the term "physiologically active carrier" refers to a physiologically active substance showing additional activities distinct to the physiological activity of the physiologically active polypeptide, which can sustain the physiological activities of the physiologically active polypeptide such as the pharmacological effects, or induce targeting to a specific site or necrosis by binding to the non-peptidyl polypeptide together with the physiologically active polypeptide.

The physiologically active carrier used in the present invention may include a substance having the aforementioned activities without any limitation, e.g., albumin, immunoglobulin Fc region, transferrin, aptamer, toxin, gelatin, collagen, dextran, polysaccharides, fatty acids, fibrinogen, or the like. Specifically, the physiologically active carrier may be an albumin, an immunoglobulin Fc region, or a transferrin, and more specifically, an immunoglobulin Fc region, but is not limited thereto.

The immunoglobulin Fc region of the present invention refers to the heavy chain constant region 2 (CH2) and the heavy chain constant region 3 (CH3) of an immunoglobulin, excluding the variable regions of the heavy and light chains, the heavy chain constant region 1 (CH1), and the light chain constant region 1 (CL1). It may further include a hinge region at the heavy chain constant region. Also, the immunoglobulin Fc region of the present invention may be an extended form containing a part or all of the Fc region including the heavy chain constant region 1 (CH1) and/or the light chain constant region 1 (CL1), except for the variable regions of the heavy and light chains, as long as it has a physiological function substantially similar to or better than the native immunoglobulin Fc, and may include immunoglobulin Fc regions modified by phosphorylation, sulfation, acrylation, glycosylation, methylation, farnesylation, acetylation, amidation, or the like. The range of immunoglobulin Fc, the preparation method thereof, and the method of covalently linking the immunoglobulin Fc to the non-peptidyl polymer-physiologically active polypeptide conjugate are disclosed in detail in Korean Patent Nos. 10-775343, 10-725314, 10-725315, and 10-824505, which are incorporated herein by reference.

In an embodiment of the present invention where the non-peptidyl polymer is site-specifically linked to a specific amino acid of the physiologically active polypeptide in the polypeptide conjugate, generation of additional conjugates other than the physiologically active polypeptide conjugate are minimized. This is beneficial for physiological activity and increasing the yield of the physiologically active polypeptide conjugate having a pharmacological value.

In a specific embodiment of the present invention, each of the imidazo-acetyl exendin-4(Lys27)-PEG conjugates prepared by the known pegylation method and the pegylation method including selective precipitation using isopropanol was linked to a human immunoglobulin Fc fragment, and purity and yield of the imidazo-acetyl-exendin-4-immunoglobulin Fc were analyzed. As a result, both conjugates had the same purity of 27.6% (Table 5), but the imidazo-acetyl exendin-4-immunoglobulin Fc conjugate prepared by the pegylation method including selective precipitation showed a higher yield than that of the conjugate prepared by the known method.

In the present invention, imidazo-acetyl-exendin-4-immunoglobulin FC is used interchangeably with CA-exendin-4-PEG-Immunoglobulin Fc or immunoglobulin FC-CA-exendin-4-PEG(Lys27).

MODE FOR THE INVENTION

Hereinafter, the present invention will be described in more detail with reference to the following Examples.

However, these Examples are for illustrative purposes only, and the invention is not intended to be limited by these Examples.

Example 1. Pegylation of Imidazo-Acetyl Exendin-4 and Separation of Positional Isomers 3.4K ALD(2) PEG (a 3.4 kDa PEG having two aldehyde groups, NOF, Japan) was used to perform pegylation at Lys of imidazo-acetyl-exendin-4 (CA-exendin-4, Bachem, USA).

To pegylate the Lys position of imidazo-acetyl-exendin-4 using 3.4K ALD(2) PEG, the peptide and PEG were reacted at a molar ratio of about 1:3 to 1:30 with a peptide concentration of about 5 mg/mL to 18 mg/mL for 0.5 hours to 4.0 hours at 4° C. to 8° C. and 20° C. to 25° C. In this regard, the reaction was allowed to proceed in a 100 mM HEPES buffer solution at a pH of 6.5 to 7.5 with addition of a reducing agent, 20 to 30 mM SCB ($NaCNBH_3$). Specific reaction conditions and a result of separation by the following method are shown in the following Tables 1 and 2. In detail, they were reacted at a peptide concentration of about 15 mg/mL for 3 hours at 4° C. to 8° C., and a result of separation by the following method is shown in FIG. 2.

Imidazo-acetyl exendin-4-PEG was separated from process related impurities such as multi-PEGylated form and unreacted form (denoted $(PEG)_n$-imidazo-acetyl exendin-4 in the table below) in each reaction solution using a SOURCE 15S column with a linear concentration gradient of KCl in a citric acid buffer solution at pH 2.0-4.0

As a result, peaks for $(PEG)_n$-imidazo-acetyl exendin-4 and imidazo-acetyl exendin-4-PEG(Lys12) were eluted earlier, and then a Lys27-pegylated peak was eluted, and a peak for the unreacted imidazo-acetyl-exendin-4 was eluted in the last portion (FIG. 2). Further, the content of $(PEG)_n$-imidazo-acetyl exendin-4+imidazo-acetyl exendin-4-PEG (Lys12) was about 10% to 40%, the content of imidazo-acetyl exendin-4-PEG was about 40% to 50%, and the content of unreacted imidazo-acetyl exendin-4 was about 10% to 50%.

Example 2. Pegylation of Insulin Analog and Separation of Positional Isomers 3.4K ALD(2) PEG was used to perform pegylation at the β chain N-terminus of an insulin analog (WO2014-133324, Hanmi Pharmaceutical Co., Ltd, Korea).

To pegylate the N-terminus position of insulin analog using 3.4K ALD(2) PEG, the peptide and PEG were reacted at a molar ratio of about 1:4 with a peptide concentration of about 5 mg/mL to 18 mg/mL for 0.5 hours to 4.0 hours at 4° C. to 8° C. and 20° C. to 25° C. In this regard, the reaction was allowed to proceed in a 50 mM sodium citrate buffer solution at a pH of 4.0 to 6.0 with addition of a reducing agent, 3-5 mM SCB ($NaCNBH_3$). In detail, they were reacted at a peptide concentration of about 5 mg/mL for 2 hours at 4° C. to 8° C., and a result of separation by the following method is shown in FIG. 3.

Insulin analog-PEG was separated from each reaction solution using a SP-HP column with a linear concentration gradient of KCl in a citric acid buffer solution at pH 2.0~4.0

As a result, peaks for $(PEG)_n$-insulin analog were eluted earlier, and then a N-terminus-pegylated peak was eluted, and a peak for the unreacted insulin analog was eluted in the last portion (FIG. 3). Further, the content of $(PEG)_n$-insulin

TABLE 1

| Reaction conditions according to pH & protein concentration | | | Fraction eluted from SOURCE S column (%) | | |
|---|---|---|---|---|---|
| pH | Concentration (mg/mL) | Reaction time (hours) | $(PEG)_n$-imidazo-acetyl exendin-4 + imidazo-acetyl exendin-4-PEG (Lys12) | Imidazo-acetyl exendin-4-PEG (Lys27) | Unreacted imidazo-acetyl exendin-4 |
| 6.5 | 5 | 4 | 15 | 37 | 50 |
|  | 12 | 4 | 17 | 43 | 27 |
| 7.5 | 5 | 4 | 12 | 41 | 44 |
|  | 12 | 4 | 30 | 44 | 26 |
|  | 15 | 3 | 25 | 45 | 30 |
|  | 18 | 4 | 43 | 40 | 17 |

TABLE 2

| Reaction conditions according to protein concentration (pH 7.5, 20° C. to 25° C., 20 mM SCB) | | Fraction eluted from SOURCE S column (%) | | |
|---|---|---|---|---|
| Protein concentration (mg/mL) | Reaction time (hours) | $(PEG)_n$-imidazo-acetyl exendin-4 + imidazo-acetyl exendin-4-PEG (Lys12) | Imidazo-acetyl exendin-4-PEG (Lys 27) | Unreacted imidazo-acetyl exendin-4 |
| 10 | 0.5 | 27 | 43 | 30 |
|  | 1 | 38 | 45 | 17 |
|  | 1.5 | 43 | 47 | 10 |
| 15 | 0.5 | 15 | 43 | 42 |
|  | 1 | 21 | 45 | 34 |
|  | 1.5 | 30 | 47 | 23 |
| 20 | 0.5 | 30 | 40 | 30 |
|  | 1 | 29 | 39 | 32 | analog was about 10% to 20%, the content of insulin analog-PEG was about 50% to 60%, and the content of unreacted insulin analog was about 5% to 20%.

Example 3. Pegylation of Imidazo-Acetyl-Exendin-4 and Separation of Non-Pegylated Imidazo-Acetyl-Exendin-4 by Selective Precipitation Using Organic Solvent 3.4K ALD(2) PEG was used to perform pegylation at the Lys position of imidazo-acetyl-exendin-4 (CA-exendin-4, Bachem, USA).

The reaction conditions are the same as in Example 1. The pegylation solution was treated with isopropanol, 1-propanol, 1-butanol, acetone, acetonitrile in 2 volumes or more, specifically, with 3 to 7 volumes of that of the reaction solution. From the organic solvent-treated reaction solution, a pegylated imidazo-acetyl-exendin-4 aqueous solution and a non-pegylated, unreacted imidazo-acetyl-exendin-4 precipitate were separated (FIG. 4). Of these, the aqueous solution was purified in the same manner as in Example 1 (FIG. 6), and the content of each purified fraction is shown in the following Table 3.

TABLE 3

| Treatment amount of isopropanol (times of pegylation solution volume) | Fraction eluted from SOURCE S column (%) | | | Recovery rate of precipitate of unreacted imidazo-acetyl exendin-4 after treatment with IPA (%) |
|---|---|---|---|---|
| | $(PEG)_n$-imidazo-acetyl exendin-4 + imidazo-acetyl exendin-4-PEG (Lys12) | Imidazo-acetyl exendin-4-PEG | Unreacted imidazo-acetyl exendin-4 | |
| none | 25 | 45 | 30 | n/a |
| 4 X | 25 | 45 | 15 | 15 |
| 5 X | 25 | 45 | 10 | 19 |
| 6 X | 25 | 45 | 8 | 22 |

In the aqueous solution, the content of $(PEG)_n$-imidazo-acetyl exendin-4+imidazo-acetyl exendin-4-PEG(Lys12) was about 10% to 40%, the content of imidazo-acetyl exendin-4-PEG was about 40% to 50%, and the content of unreacted imidazo-acetyl exendin-4 was about 5% to 15%. Further, the content of the separated imidazo-acetyl-exendin-4 precipitate was 15% to 30% (Table 3).

Example 4. Pegylation of Insulin Analog and Separation of Non-Pegylated Insulin Analog by Selective Precipitation Using Organic Solvent 3.4K ALD(2) PEG (PEG having two aldehyde groups, NOF, Japan) was used to perform pegylation at N-terminus of insulin analog (Hanmi Pharmaceutical Co., Ltd, Korea) β chain.

The reaction conditions are the same as in Example 2. The pegylation solution was treated with isopropanol, ethanol, 1-propanol, acetone, acetonitrile in 2 volumes or more, specifically, with 3 to 7 volumes of that of the reaction solution. From the organic solvent-treated reaction solution, a pegylated insulin analog solution and a non-pegylated, unreacted insulin analog precipitate were separated (FIG. 5). Of these, the aqueous solution was purified in the same manner as in Example 2 (FIG. 9).

Example 5. Re-Pegylation of Selective Precipitate of Non-Pegylated Imidazo-Acetyl Exendin-4 and Separation of Positional Isomers 3.4K ALD(2) PEG (PEG having two aldehyde groups, NOF, Japan) was used to perform pegylation at the Lys position of imidazo-acetyl-exendin-4 (CA-exendin-4, Bachem USA) and about 20% to 30% of an imidazo-acetyl-exendin-4 precipitate which was separated by performing selective precipitation using isopropanol in the same manner as in Example 3 was recycled and subjected to pegylation.

To pegylate Lys of the imidazo-acetyl-exendin-4 precipitate using 3.4K ALD(2) PEG, an imidazo-acetyl-exendin-4 precipitate and PEG were reacted at a molar ratio of 1:7.5 for 0.5 hours to 2.0 hours at 20° C. to 25° C. at an imidazo-acetyl-exendin-4 precipitate-redissolving solution concentration of about 15 mg/mL. In this regard, the reaction was allowed to proceed in a 100 mM HEPES buffer solution at pH 7.5 with addition of a reducing agent, 20 mM SCB ($NaCNBH_3$). Purification was performed in the same manner as in Example 1. A result of purifying the re-pegylation solution of a non-pegylated imidazo-acetyl exendin-4 precipitate shows that the content of $(PEG)_n$-imidazo-acetyl exendin-4+imidazo-acetyl exendin-4-PEG(Lys12) was about 15% to 40%, the content of imidazo-acetyl exendin-4-PEG was 40% to 50%, and the content of unreacted imidazo-acetyl exendin-4 was about 10% to 40% (FIG. 7), which are similar to the primary pegylation result (Table 2).

Example 6. Re-Pegylation of Selective Precipitate of Non-Pegylated Insulin Analog and Separation of Positional Isomers 3.4K ALD(2) PEG was used to perform pegylation at N-terminus of insulin analog (Hanmi Pharmaceutical Co., Ltd, Korea) β chain, and about 0.5% to 10% of precipitates which were separated by performing selective precipitations using isopropanol in the same manner as in Example 4 were recycled and subjected to pegylation.

To pegylate N-terminus of the insulin analog precipitate using 3.4K ALD(2) PEG, an insulin analog precipitate and PEG were reacted at a molar ratio of 1:4 for 0.5 hours to 4.0 hours at 4° C. to 8° C. at an insulin analog precipitate-redissolving solution concentration of about 5-18 mg/mL. In this regard, the reaction was allowed to proceed in a 50 mM sodium citrate buffer solution at pH 4.0 to 6.0 with addition of a reducing agent, 3-5 mM SCB ($NaCNBH_3$). Purification was performed in the same manner as in Example 2. A result of purifying the re-pegylation solution of a non-pegylated precipitate shows that the content of $(PEG)_n$-insulin analog was about 0% to 15%, the content of insulin analog-PEG was 20% to 40%, and the content of unreacted insulin analog was about 30% to 45% (FIG. 10).

Example 7. Yield after Separation of Positional Isomers from Mixture of Pegylated Imidazo-Acetyl Exendin-4 Aqueous Solution and Re-Pegylated Precipitate 3.4K ALD(2) PEG was used to perform pegylation at the Lys position of imidazo-acetyl-exendin-4 (CA-exendin-4, Bachem USA). The reaction was performed in the same manner as in Example 1, and the reaction solution was subjected to selective precipitation by treatment with iso-propanol in the same manner as in Example 3. The resulting precipitate was re-pegylated in the same manner as in Example 5. The iso-propanol-treated aqueous solution and the re-pegylated precipitate were mixed and purified in the same manner as in Example 1 to separate positional isomers (FIG. 8).

As a result, the content of $(PEG)_n$-imidazo-acetyl exendin-4+imidazo-acetyl-exendin-4(Lys12)-PEG was about 25% to 30%, the content of imidazo-acetyl-exendin-4-PEG was about 50% to 60%, and the content of unreacted imidazo-acetyl exendin-4 was 10% to 20%.

Further, results of comparing the yield of the imidazo-acetyl-exendin-4-PEG conjugate prepared by the selective precipitation-applied pegylation method to that of the known pegylation method are given in FIG. 11 and the following Table 4. As a result, the yield of the imidazo-acetyl-exendin-4-PEG conjugate prepared by the selective precipitation-applied pegylation method was much higher than that of the known pegylation method.

TABLE 4

| Pegylation conditions | Yield of CA exendin-4-PEG (%) |
|---|---|
| Known pegylation | 100 |
| Selective precipitation-applied pegylation | 132 |

Example 8. Purity after Separation of Imidazo-Acetyl Exendin-4 Pegylated Positional Isomer To examine difference in purity between the imidazo-acetyl exendin-4 conjugates prepared by the known pegylation method and the pegylation method including selective precipitation using isopropanol, the eluted solutions of Examples 1 and 7 were used to perform reverse phase (RP) HPLC (FIGS. 12 and 13).

As a result, imidazo-acetyl exendin-4 conjugates of Example 1 according to the known method and Example 7 according to the selective precipitation-applied pegylation method showed the same purity of 97% (Table 5).

TABLE 5

| | Purity (%) | | | |
|---|---|---|---|---|
| | CA exendin-4-PEG (Lys27) column eluate after pegylation | | | Coupling solution |
| | | Control of pegylation | | |
| Conditions | RP | K12 | K27 | RP |
| Known pegylation | 97.0 | 0.4 | 97.6 | 27.6 |
| Selective precipitation-applied pegylation | 97.0 | 0.1 | 97.4 | 27.6 |

Example 9. Lys-C Peptide Mapping after Separation of Imidazo-Acetyl Exendin-4 Pegylated Positional Isomer To examine the conjugation site of PEG at imidazo-acetyl-exendin-4, imidazo-acetyl-exendin-4 was digested with a protease lysine-C, and analyzed by reverse phase chromatography. The experiment was performed as follows: PEG conjugates purified in Examples 1 and 7 and imidazo-acetyl-exendin-4 were dissolved in a triethylamine-HCl buffer solution (10 mmol/L; pH 7.5) at a concentration of 1 mg/mL, and then 10 ?L of enzyme (0.1 mg/mL) was added to allow reaction at 37° C. for 4 hours. After completion of the reaction, the reaction mixtures were analyzed by reverse phase chromatography (FIGS. 14 and 15).

As a result, purities of the pegylated positional isomers according to each reaction are given in Table 5, and purified PEG conjugates of Examples 1 and 7 had similar purity (Table 5), respectively.

Example 10. Preparation of Imidazo-Acetyl Exendin-4-Immunoglobulin Fc Conjugate To prepare an imidazo-acetyl exendin-4-immunoglobulin Fc conjugate, the imidazo-acetyl-exendin-4-PEG conjugate obtained in Example 1 was conjugated with a human immunoglobulin Fc fragment purchased from Hanmi Pharmaceutical Co., Ltd. The imidazo-acetyl-exendin-4(Lys27)-PEG conjugate and immunoglobulin Fc were reacted at a molar ratio of 1:2.5 with a total protein concentration of about 10 mg/mL at 4° C. to 8° C. for 12 hours to 16 hours. The reaction solution was 100 mM HEPES at pH 8.2, and treated with 3% Triton X-100 and a reducing agent, 50 mM NaCNBH$_3$. After the coupling reaction, the result of reverse phase HPLC analysis of the coupling reaction solution (FIG. 16) shows that purity of an imidazo-acetyl exendin-4-immunoglobulin Fc conjugate was 27.6% (Table 5).

Example 11. Preparation of Imidazo-Acetyl Exendin-4-Immunoglobulin Fc Conjugate by Application of Selective Precipitation The imidazo-acetyl exendin-4(Lys27)-PEG conjugate obtained in Example 7 was conjugated with a human immunoglobulin Fc fragment purchased from Hanmi Pharmaceutical Co., Ltd (Korea). Coupling was performed in the same manner as in Example 10, and purity was analyzed. The result of reverse phase HPLC analysis of the reaction solution (FIG. 17) shows that its purity was 27.6% (Table 5). The effect of yield improvement of the imidazo-acetyl exendin-4-immunoglobulin Fc conjugate of Example 7 was compared with the yield of Example 1, and the result is shown in FIG. 18 and the following Table 6. As a result, the yield of the imidazo-acetyl exendin-4-PEG conjugate prepared by the selective precipitation-applied pegylation method was higher than that of the known method. Therefore, it can be seen that, when the imidazo-acetyl exendin-4-PEG conjugate prepared by the selective precipitation-applied pegylation method is used to prepare the imidazo-acetyl exendin-4-immunoglobulin Fc conjugate, the yield is higher than that of the known pegylation method.

TABLE 6

| Pegylation conditions | Yield of imidazo-acetyl exendin-4-immunoglobulin Fc conjugate (%) |
|---|---|
| Known pegylation | 100 |
| Selective precipitation-applied pegylation | 128 |

Example 12. Lysine-C Peptide Mapping for Analysis of Purity of Imidazo-Acetyl Exendin-4 According to Application of Selective Precipitation (by Use of Isopropanol)

To examine changes in the status of imidazo-acetyl exendin-4 before and after treatment with isopropanol, lysine-C peptide mapping was performed. FIG. 19 shows a result of mapping imidazo-acetyl exendin-4 before treatment with isopropanol, and FIG. 20 shows a result of mapping imidazo-acetyl exendin-4 after application of selective precipitation (treatment with isopropanol). As a result, there was no change before and after treatment. The analysis was performed in the same manner as in Example 9.

Example 13. LC-Mass for Analysis of Purity of Imidazo-Acetyl Exendin-4 According to Application of Precipitation (by Use of Isopropanol)

To examine a protein sequence as a primary structure of imidazo-acetyl exendin-4 before and after treatment with isopropanol, LC-Mass was performed. As a result, there was no change in the primary structure before and after application of selective precipitation (isopropanol treatment) (FIG. 21).

Example 14. CD Spectroscopy for Analysis of Secondary Structure of Imidazo-Acetyl Exendin-4 According to Application of Precipitation (by Use of Isopropanol)

To examine changes in a secondary structure of imidazo-acetyl exendin-4 before and after treatment with isopropanol (IPA), CD spectroscopy was performed. As a result, there was no change in the content of the secondary structure before and after application of selective precipitation (isopropanol treatment) (FIG. 22 and Table 7).

TABLE 7

| | Content (%) (UV range: 190 nm to 260 nm) | |
|---|---|---|
| Secondary structure | CA-exendin 4 before IPA treatment | Recycled CA-exendin 4 after IPA treatment |
| Helix | 33.1 | 33.5 |
| Anti-parallel | 11.2 | 10.9 |
| Parallel | 7.8 | 7.7 |
| Beta-Turn | 17.5 | 17.4 |
| Random coil | 27.6 | 27.1 |
| Total | 97 | 96.6 |

Example 15. Measurement of In Vitro Activity of Imidazo-Acetyl Exendin-4 Before and after Application of Selective Precipitation To measure efficacy of a long-acting formulation of imidazo-acetyl exendin-4 before and after treatment with isopropanol, in vitro cell activity was measured. A method of measuring in vitro cell activity of GLP-1 is to measure an increase in intracellular cAMP by treating GLP-1 receptor-cloned CHO cells with GLP-1.

The method of measuring in vitro cell activity used in this experiment was performed by treating CHO/GLP-1 with exendin-4 and test materials by varying concentrations thereof and then measuring cAMP levels to compare $EC_{50}$ values. As a control group of imidazo-acetyl exendin-4 after treatment with isopropanol, imidazo-acetyl exendin-4 before treatment with isopropanol was used. A result of measuring in vitro activity is shown in FIG. 23 and Table 8. As a result, there was no difference in the activity between imidazo-acetyl exendin-4 conjugates before and after treatment with iso-propanol.

TABLE 8

| Sample | $EC_{50}$ (nM) | Relative activity (% vs. original batch) |
|---|---|---|
| CA-exendin 4 before treatment of 2-propanol | 2.41 ± 0.19 | 100.0 (ns) |
| Recycled CA-exendin 4 after treatment of 2-propanol | 2.32 ± 0.26 | 103.8 (ns) | ns, no significance
p > 0.05 by T-test

Historical Range
1) CA Exendin-4: 1.85 nm to 2.33 nm

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

The invention claimed is:

1. A method of preparing a physiologically active polypeptide conjugate, the method comprising:
   (1) precipitating from a reaction mixture a physiologically active polypeptide unconjugated to a non-peptidyl polymer using an organic solvent,
   wherein the reaction mixture comprises: (i) the physiologically active polypeptide; and (ii) the physiologically active polypeptide conjugate,
   wherein the physiologically active polypeptide is imidazo-acetyl(CA)-exendin-4,
   wherein said reaction mixture is the product of a reaction conjugating the non-peptidyl polymer to an amino acid residue of the physiologically active polypeptide, and
   wherein the organic solvent is isopropanol, 1-propanol, 1-butanol, acetone, or acetonitrile; and
   (2) reacting the physiologically active polypeptide recovered from the precipitate with the non-peptidyl polymer under the conjugation reaction of step (1),
   wherein the non-peptidyl polymer is a polyethylene glycol, and
   wherein the polyethylene glycol has a nominal molecular weight of 3,400 Da.

2. The method of claim 1, wherein step 2) comprises dissolving the precipitated physiologically active polypeptide and then conjugating the polypeptide to the non-peptidyl polymer.

3. The method of claim 1, wherein the reaction mixture in step 1) comprises, based on the total weight of the reaction mixture, 10% by weight or more of the unconjugated physiologically active polypeptide.

4. The method of claim 1, wherein the organic solvent is isopropanol.

5. The method of claim 4, wherein the reaction mixture in step 1) is treated with 2 to 7 volumes of isopropanol.

6. The method of claim 5, wherein the reaction mixture in step 1) is treated with 3 to 7 volumes of isopropanol.

7. The method of claim 1, wherein in step 2), the recovered physiologically active polypeptide is reacted with the non-peptidyl polymer for 0.5 hours to 4 hours.

8. The method of claim 1, wherein the non-peptidyl polymer is conjugated to Lys27 of imidazo-acetyl(CA)-exendin-4.

9. The method of claim 1, wherein the non-peptidyl polymer comprises at least one reactive group selected from the group consisting of an aldehyde group, a propionaldehyde group, a butyraldehyde group, a maleimide group, and a succinimide derivative.

10. The method of claim 9, wherein the non-peptidyl polymer has an aldehyde group as a reactive group.

11. The method of claim 10, wherein the aldehyde group is a propionaldehyde group.

12. The method of claim 1, further comprising purifying the physiologically active polypeptide conjugate after step 2).

13. The method of claim 12, wherein the purification is performed using ion exchange chromatography.

14. The method of claim 13, wherein the ion exchange chromatography is high pressure ion exchange chromatography.

15. A method of preparing a conjugate of a physiologically active polypeptide and a physiologically active carrier, the method comprising conjugating via a covalent bond, the physiologically active polypeptide conjugate prepared according to claim 1 with a physiologically active carrier to prepare a polypeptide-carrier conjugate, wherein in the polypeptide-carrier conjugate, the two ends of the non-peptidyl polymer are respectively conjugated to the physiologically active carrier and the physiologically active polypeptide.

16. The method of claim 15, wherein the physiologically active carrier is selected from the group consisting of albumin, an immunoglobulin Fc region, transferrin, aptamer, toxin, gelatin, collagen, dextran, polysaccharide, fatty acid, and fibrinogen.

17. The method of claim 16, wherein the physiologically active carrier is an immunoglobulin Fc region.

* * * * *